US006624245B2

(12) United States Patent
Wallace et al.

(10) Patent No.: US 6,624,245 B2
(45) Date of Patent: Sep. 23, 2003

(54) RAPID-GELLING BIOCOMPATIBLE POLYMER COMPOSITION AND ASSOCIATED METHODS OF PREPARATION AND USE

(75) Inventors: Donald G. Wallace, Menlo Park, CA (US); Gregory M. Cruise, Fremont, CA (US); Woonza M. Rhee, Palo Alto, CA (US); Jacqueline Anne Schroeder, Boulder Creek, CA (US); George T. Coker, III, Castro Valley, CA (US); Marcee M. Maroney, Portola Valley, CA (US); Olof Mikael Trollsas, Los Gatos, CA (US)

(73) Assignee: Cohesion Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/012,263

(22) Filed: Nov. 5, 2001

(65) Prior Publication Data

US 2002/0165337 A1 Nov. 7, 2002

Related U.S. Application Data

(63) Continuation-in-part of application No. 09/293,708, filed on Apr. 16, 1999, now Pat. No. 6,312,725.

(51) Int. Cl.[7] ...................... C08F 283/00; C08G 63/91; C08G 69/48
(52) U.S. Cl. ...................... 525/54.1; 525/419; 525/420; 525/425; 604/891.1
(58) Field of Search ............................... 525/54.1, 419, 525/420, 425; 604/891.1

(56) References Cited

U.S. PATENT DOCUMENTS

| | | | |
|---|---|---|---|
| 5,292,362 A | 3/1994 | Bass et al. | |
| 5,385,606 A | 1/1995 | Kowanko | |
| 5,410,016 A | 4/1995 | Hubbell et al. | |
| 5,496,872 A | 3/1996 | Constancis et al. | |
| 5,514,379 A | 5/1996 | Weissleder et al. | |
| 5,583,114 A | 12/1996 | Barrows et al. | |
| 5,618,551 A | 4/1997 | Tardy et al. | |
| 5,629,294 A | 5/1997 | DiZerega et al. | |
| 5,874,500 A | 2/1999 | Rhee et al. | |
| 6,166,130 A | * 12/2000 | Rhee et al. | 525/54.1 |
| 6,323,278 B2 | * 11/2001 | Rhee et al. | 525/54.1 |

FOREIGN PATENT DOCUMENTS

| | | |
|---|---|---|
| DE | 2809799 A1 | 9/1978 |
| EP | 0841359 A1 | 5/1998 |
| EP | 0841360 A1 | 5/1998 |
| EP | 0841361 A1 | 5/1998 |
| WO | WO 90/05755 | 5/1990 |
| WO | WO 97/22371 | 6/1997 |
| WO | WO 00/62827 | 10/2000 |

OTHER PUBLICATIONS

Bentley (1998), "PEG Derivatives of Small Drug Molecules," *Shearwater Polymers, Inc.* 1(3).

Bodanszky (1993), *Principles of Peptide Synthesis*, 2 Ed., Springer–Verlog, Berlin, p. 21–37.
Braatz et al. (1992), "A New Hydirophihc Polymer for Biomaterial Coatings with Low Protein Adsorption," *J. Biomater, Sci. Polymer Edn.* 3(6):451–462.
Ellis et al. (1990), "The Ideal Tissue Adhesive in Facial Plastic and Reconstructive Surgery," J. of *Otolaryngol* 19:68–72.
Gelest, Inc. (1995), brochure, Tullytown, PA.
Hanis et al. (1992), "Synthesis of New Poly(Ethylene Glycol) Derivatives," *Poly(Ethylene Glycol) Chemistry: Biotechnical and Biomedical Applications*, Chapter 22, pp. 371–380, Harris, Ed., Plenum Press, New York, NY.
Hendrick et al. (1998), "Dendrimer–like Star Block and Amphiphilic Copolymers by Combination of Ring Opening and Atom Transfer Radical Polymerization," *Macromolecules* 31:8691–8705.
Hubbell (1995), "Biomaterials in Tissue Engineering," *Bio/Technology* 13:565–576.
Keys et al. (1998), "Poly(ethylene glycol) Star Polymer Hydrogels," *Macromolecules* 31:8149–8156.
Leach et al. (1990), "Reduction of Postoperative Adhesions in the Rat Uterine Horn Model with Poloxamer 407," *Am. J. Obstet. Gynecol.* 162:1317–1319.
Lin et al. (1998), "Thermosensitive Lactitol–Based Polyether Polyol (LPEP) Hydrogels," *Journal of Polymer Science: Part A: Polymer Chemistry* 36:979–984.
Lundblad (1991), "The Modification of Cysteine," *Chemical Reagents for Protein Modification*, $2^{nd}$ $^{Ed.}$.Chapter 6, pp. 59–93, CRC Press, Boca Raton, FL.
Rempp et al. (1990), "Anionically Polymerized Star Macromolecules Having Divinylbenzene Cores with Grafted Poly (Ethylene Oxide) Arms as Biomaterials," *American Chemical Society, Polymer Division Symposium*, p. 12, Boston, MA.

* cited by examiner

Primary Examiner—Nathan M. Nutter
(74) Attorney, Agent, or Firm—Dianne K. Reed; Reed & Eberle LLP

(57) ABSTRACT

A method is provided for the rapid formation of a biocompatible gel, and may be carried out in situ, i.e., at a selected site within a patient's body. The method involves admixing a biocompatible crosslinking component A having m sulfhydryl groups wherein m≧2 and a biocompatible crosslinking component B having n sulfhydryl-reactive groups wherein n≧2 and m+n>4, wherein the sulfhydryl-reactive groups are capable of covalent reaction with the sulfhydryl groups upon admixture of the components under effective crosslinking conditions to form a gel in less than one minute. Suitable reaction conditions for carrying out the crosslinking reaction will depend on the particular components and the type of reaction involved; that is, the "effective crosslinking conditions" may involve reaction in bulk or in a solvent, addition of a base, and/or irradiation of the admixture in the presence of a free radical initiator. Exemplary uses include tissue augmentation, biologically active agent delivery, bioadhesion, and prevention of adhesions following surgery or injury. Reactive gel-forming compositions and systems are also provided.

47 Claims, 4 Drawing Sheets

RAPID-GELLING BIOCOMPATIBLE POLYMER COMPOSITION AND ASSOCIATED METHODS OF PREPARATION AND USE

CROSS-REFERENCE TO RELATED APPLICATIONS

This application is a continuation-in-part of U.S. application Ser. No. 09/293,708, filed Apr. 16, 1999, and now U.S. Pat. No. 6,312,725 the disclosure of which is incorporated herein by reference.

TECHNICAL FIELD

This invention relates generally to biocompatible polymer compositions that rapidly crosslink to form a gel. More particularly, the invention relates to a composition prepared by admixture of individually reactive polymer components, wherein the admixture initiates rapid crosslinking and gel formation. Such compositions are particularly well suited for use in a variety of tissue-related applications in which rapid adhesion to the tissue and gel formation is desired. Accordingly, the invention additionally relates to methods of using the compositions as bioadhesives, for tissue augmentation, in the prevention of surgical adhesions, for coating surfaces of synthetic implants, as drug delivery matrices, for ophthalmic applications, and in other applications, as discussed herein and/or as appreciated by one of ordinary skill in the art.

BACKGROUND OF THE INVENTION

The use of polymer compositions in tissue engineering is now widely recognized, particularly those compositions manufactured with synthetic polymers. In contrast to many naturally derived compositions, synthetic polymer compositions can be formulated to exhibit predetermined physical characteristics, such as gel strength, as well as biological characteristics, such as biodegradability.

In a variety of tissue engineering applications, it is desirable to use compositions that can be administered as liquids, but which subsequently form gels at the site of administration. Such in situ gel-forming compositions are convenient to use since they can be administered as liquids from a variety of different devices, and are adaptable for administration to any site, since they are not preformed. Many different mechanisms have been described that can be used to promote gel formation in situ. For example, photoactivatable mixtures of water-soluble co-polyester prepolymers and polyethylene glycol have been described as useful in the preparation of gel barriers and drug release matrices. In another approach, block copolymers of a Pluronic™ poloxamer have been designed that are soluble in cold water, but form insoluble gels that adhere to tissues at body temperature (Leach et al. (1990) *Am. J. Obstet. Gynecol.* 162: 1317–1319 (1990)). Polymerizable cyanoacrylates have also been described for use as tissue adhesives (Ellis, et al. (1990) *J. Otolaryngol.* 19:68–72 (1990). In yet another approach, two-part synthetic polymer compositions have been described that, when mixed together, form covalent bonds with one another, as well as with exposed tissue surfaces. (PCT WO 97/22371, which corresponds to U.S. application Ser. No. 08/769,806.) In a similar approach involving a two-part composition, a mixture of a protein and a bifunctional crosslinking agent has been described for use as a tissue adhesive (U.S. Pat. No. 5,583,114.) One difficulty encountered when designing in situ gel forming compositions is that optimizing the composition to enhance gel formation may worsen tissue inflammation at the site of administration. A possible explanation for this effect is that highly reactive composition components that are capable of rapid gel formation may adversely affect tissue surfaces.

The compositions of the present invention have been formulated to provide for rapid gelation, while decreasing the likelihood and/or severity of tissue inflammation at the site of administration relative to that associated with the previously described compositions.

SUMMARY OF THE INVENTION

Accordingly, in one aspect of the invention, a reactive polymer composition is provided that comprises an admixture of two or more biocompatible, reactive components selected so as to rapidly react with each other to form a crosslinked gel. The first component, component "A," is a sulfhydryl-containing component having m sulfhydryl groups, and the second component, component "B," is a sulfhydryl-reactive component B having n sulfhydryl-reactive groups capable of reaction with the m sulfhydryl groups to form covalent bonds, wherein $m \geq 2$ and $n \geq 2$, and generally the sum of $m+n \geq 4$. Preferably, at least one of m and $n \geq 3$, and more preferably, m and n are each $\geq 4$; in this way, sufficient reactivity for rapid formation of a three-dimensional polymeric gel is ensured. For extremely fast-reacting compositions, both m and n are each $\geq 12$. The compositions may be used either in situ or ex situ, to give a biocompatible crosslinked gel having utility in a host of different contexts, e.g., in bioadhesion, biologically active agent delivery, tissue augmentation, and other applications. The preferred context, however, involves crosslinking and gelation in situ.

The reaction conditions necessary for the rapid crosslinking reaction to take place will depend on the particular components A and B. When neither component is a liquid at room temperature, the reaction must be carried out in an added solvent, preferably a sterile aqueous medium. If at least one of the components is a liquid and capable of serving as a reaction solvent, the reaction may be conducted "neat" (also referred to as "in bulk"), i.e., no added solvent is necessary. In addition, for components that crosslink via a nucleophilic substitution mechanism, such that covalent bonds are formed by nucleophilic attack of the sulfhydryl groups on electrophilic sulfhydryl-reactive groups, an added base is typically necessary to increase the nucleophilicity of the sulfhydryl groups such that the crosslinking reaction occurs sufficiently rapidly. For components that crosslink via other mechanisms, an added base is generally not required (although one may be present). For example, reaction of unconjugated olefins with sulfhydryl groups does not involve nucleophilic substitution, but rather requires light or other radiation effective to generate the sulhydryl radical R—S—, and a suitable free radical initiator.

The components of the composition will generally be admixed, under the reaction conditions appropriate to promote rapid crosslinking of the selected components, e.g., in bulk, in an aqueous liquid, with added base, and/or in the presence of radiation and/or a free radical initiator), immediately prior to administration. Alternatively, the components may be individually applied to the site of administration under appropriate reaction conditions, such that admixture occurs at the administration site.

It will be appreciated that more than one sulfhydryl-containing component and/or more than one sulfhydryl-reactive component may be present in the reactive composition.

At least one of the reactive components A and B is a polymer, preferably a hydrophilic polymer, and may be naturally occurring, purely synthetic, or semisynthetic polymer, wherein "semi-synthetic" refers to a chemically modified naturally occurring polymer. The non-reactive portion of the polymer is referred to as its "core," with either sulhydryl groups or sulfhydryl-reactive groups bound thereto. Suitable polymer cores include synthetic polymers, as noted above, polyamino acids, polysaccharides, and the like. The molecular weight of the polymer can vary depending on the desired application. In most instances, the weight average molecular weight is about 100 to about 2,000,000, preferably about 1,000 to 1,000,000, more preferably about 1,000 to about 100,000, and most preferably about 1,000 to about 20,000. When the polymer core is polyethylene glycol, the preferred molecular weight is in the range of about 1000 to about 20,000, optimally about 10,000.

One or more of the reactive components in the composition may be a low molecular weight crosslinking agent, although it is preferred that not more than one of the components is comprised of such an agent. Typical low molecular weight crosslinking agents are comprised of a hydrocarbyl moiety containing 2 to 14 carbon atoms and at least two functional groups, i.e., sulfhydryl groups or sulfhydryl-reactive groups. Generally, although not necessarily, any low molecular weight component that is employed serves as the sulfhydryl-reactive component rather than as the sulfhydryl-containing component, and is used in conjunction with a thiolated polymer.

The sulfhydryl groups and the sulfhydryl-reactive groups may be directly bound to the component, indirectly bound to the component through a linking group, or indirectly bound through an extended linking moiety termed a "chain extender." Chain extenders can activate or suppress reactivity of the functional groups, and can also be used to provide sites for hydrolysis or degradation. Suitable chain extenders include poly(amino acids), poly(lactones), poly (anhydrides), poly(orthoesters), poly(orthocarbonates), poly (phosphoesters), poly(alkylene oxides) and enzymatically cleavable peptide groups.

The compositions of the present invention form gels with gel times of less than 1 minute, preferably less than 30 seconds, and most preferably less than 15 seconds. The strength (i. e., elastic modulus or G') of the resultant gels depends on the application for which the composition is adapted, but is generally in the range of about 1 N/cm$^2$ to about 100 N/cm$^2$, preferably in the range of about 1 N/cm$^2$ to 20 N/cm$^2$ for a soft gel, or in the range of about 40 N/cm$^2$ to about 100 N/cm$^2$ for a harder gel.

In addition to the reactive components, the reactive compositions of the invention may include additional materials as well, such as glycosaminoglycans, proteins such as collagen, nucleotidic materials such as DNA, cells, hemostatic agents, genes, therapeutic agents, antibiotics, growth factors, and the like.

When the sulfhydryl-reactive component is such that a base is required for the reaction between the sulfhydryl and sulfhydryl-reactive groups to occur, the components of the composition will generally be admixed in an aqueous medium having a pH in the range of about 7.5 to about 11, immediately prior to administration. Alternatively, as above, the components may be individually applied to the site of administration, such that admixture occurs at the administration site, providing that the admixture is in an aqueous medium having a pH in the range of about 7.5 to 11. It is also possible to apply such components in premixed but inactive form—i.e., in an acidic aqueous medium—and then activate them, with base, either at the site of administration or immediately before application. Preferred bases are generally, although not necessarily, non-nucleophilic.

Analogously, when the sulfhydryl-reactive component is such that the crosslinking reaction requires light or other radiation and a free radical initiator, the components may be activated, i.e., with light or other suitable radiation, either immediately prior to or following administration.

In another aspect of the invention, then, a method is provided for the formation of a biocompatible crosslinked gel in situ, wherein the method comprises:

(a) admixing (i) a biocompatible crosslinking component A having m sulfhydryl groups wherein m≧2, (ii) a biocompatible crosslinking component B having n sulfhydryl-reactive groups, wherein n≧2, capable of undergoing a nucleophilic substitution reaction with the m sulfhydryl groups upon admixture of components A and B so as to form a gel in less than one minute, and optionally (iii) at least one pH-adjusting agent, to provide a reactive composition, wherein the at least one pH-adjusting agent, if used, provides the reactive composition with a pH in the range of about 7.5 to about 11; and (b) allowing the components to react, so as to crosslink and form a gel.

Unless one or both components are liquids at the reaction temperatures employed (generally ambient temperature up to body temperature), the reaction is carried out in a solvent, preferably a sterile aqueous medium, in which case the aforementioned method further includes admixing (i), (ii) and optionally (iii) with (iv) a solvent.

In a related embodiment, wherein the components are contained in an inactive form and then activated with base prior to use, the method comprises:

(a) providing, in an aqueous medium having a pH in the range of about 3 to 6, a biocompatible crosslinking component A having m sulfhydryl groups, wherein m≧2, and a biocompatible crosslinking component B having n sulfhydrl-reactive groups wherein n≧2, and further wherein the sulfhydryl-reactive groups are capable of undergoing a nucleophilic substitution reaction with the m sulfhydryl groups upon admixture of components A and B in a basic aqueous medium, so as to form a gel in less than one minute;

(b) increasing the pH of the aqueous medium to a pH in the range of about 7.5 to about 11, by adding at least one basic reagent to the aqueous medium; and (c) allowing the components to react, so as to crosslink and form a gel.

In still another aspect of the invention, a method is provided for the formulation of a biocompatible crosslinked gel in situ, wherein the method comprises:

(a) admixing (i) a biocompatible crosslinking component A having m sulfhydryl groups wherein m≧2, (ii) a biocompatible crosslinking component B having n sulfhydryl-reactive groups, wherein n≧2, capable of undergoing a free radical coupling reaction with the m sulfhydryl groups upon admixture of components A and B in the presence of light or other radiation, and (iii) a free radical initiator;

(b) irradiating the admixture prepared in (a); and (c) allowing the components to react, so as to crosslink and form a gel.

Again, unless one or both components are liquids at the reaction temperatures employed (generally ambient temperature up to about body temperature), the reaction is carried out in a solvent, preferably a sterile aqueous medium, in which case the aforementioned method further includes admixing (i) and (ii) with (iii) such a solvent.

In another embodiment, a gel-forming system is provided in which the components are not admixed, but are physically separated. For example, the gel-forming system may be comprised of:

(a) a biocompatible crosslinking component A having m sulfhydryl groups wherein m≧2, in a liquid medium having an alkaline pH; and (b) a biocompatible crosslinking component B having n sulfhydryl-reactive groups, wherein n≧2, in either a liquid medium having a neutral or acidic pH or in powder form, and further wherein the sulfhydryl-reactive groups are capable of undergoing a nucleophilic substitution reaction with the m sulfhydryl groups upon admixture of components A and B in the presence of base.

In other aspects of the invention, methods of using the compositions encompassed by the present invention are provided, including drug delivery methods, bioadhesion, delivery of cells and genes, tissue augmentation, prevention of adhesions following surgery or injury, and implant coating. Other methods of use are also within the scope of the invention, as will be described below.

DETAILED DESCRIPTION OF THE INVENTION

I. Definitions and Overview

Figure 1:
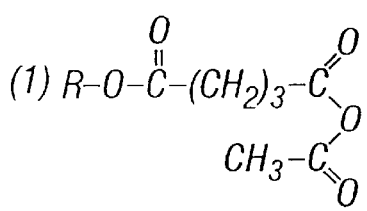
FIG. 1 depicts the structures of various sulfhydryl-reactive groups, with "R" representing the chemical structure to which the reactive group is attached.
Figure 1:
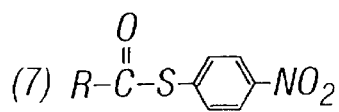
Figure 1:
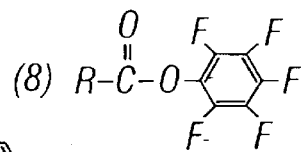
Figure 1:
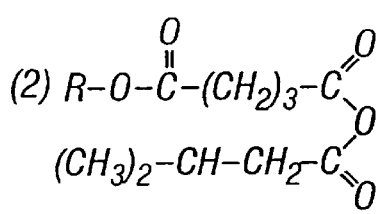
Figure 1:
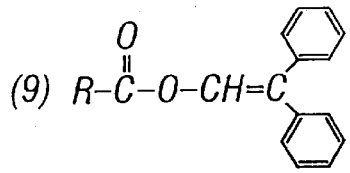
Figure 1:
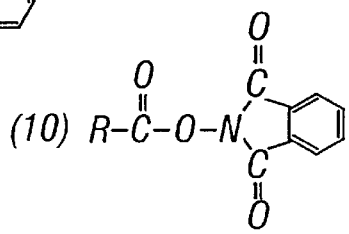
Figure 1:
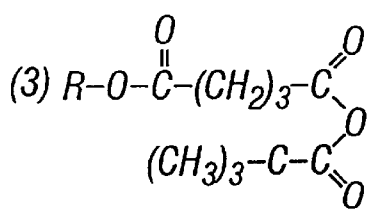
Figure 1:
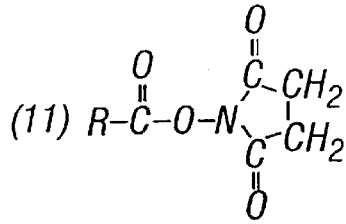
Figure 1:
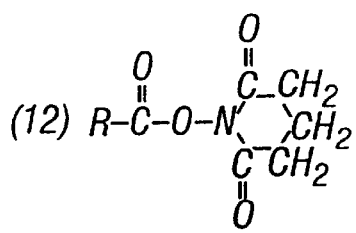
Figure 1:
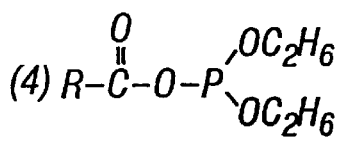
Figure 1:
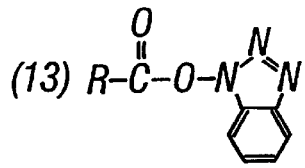
Figure 1:
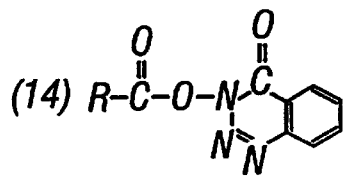
Figure 1:
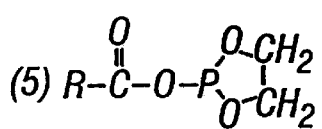
Figure 1:
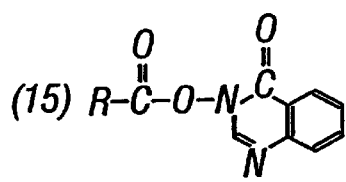
Figure 1:
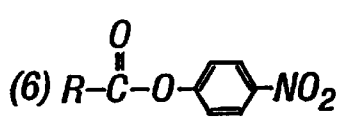

Before describing the present invention in detail, it is to be understood that unless otherwise indicated this invention is not limited to particular compositional forms, crosslinkable components, crosslinking techniques, or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a sulfhydryl-containing component" refers not only to a single sulfhydryl-containing component but also to a combination of two or more different sulfhydryl-containing components, a sulfhydryl-reactive component" refers not only to a single sulfhydryl-reactive component but also to a combination of two or more different sulfhydryl-reactive components, "a polymer" refers to a combination of polymers as well as to a single polymer, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. All patents, patent applications and other publications mentioned herein are incorporated herein by reference. Specific terminology of particular importance to the description of the present invention is defined below.

The term "crosslinked" herein refers to a composition containing intermolecular crosslinks and optionally intramolecular crosslinks as well, arising from the formation of covalent bonds. Covalent bonding between two crosslinkable components may be direct, in which case an atom in one component is directly bound to an atom in the other component, or it may be indirect, through a linking group. A crosslinked gel or matrix may, in addition to covalent bonds, also include intermolecular and/or intramolecular noncovalent bonds such as hydrogen bonds and electrostatic (ionic) bonds. The term "crosslinkable" refers to a component or compound that is capable of undergoing reaction to form a crosslinked composition.

The term "sulfhydryl-containing component" refers to a chemical compound that contains sulfhydryl (—SH) groups.

The term "sulfhydryl-reactive component" refers to a chemical compound that contains functional groups that react with sulfhydryl moieties to form a covalent bond therebetween. The sulfhydryl-reactive component may react with sulfhydryl groups as an electrophile in a nucleophilic substitution reaction (wherein the sulfhydryl groups are the nucleophiles), or it may react with sulfhydryl groups in a free radical reaction, the latter requiring a radical initiator and/or radiation, typically ultraviolet radiation.

The term "gel" refers to a state of matter between liquid and solid, and is generally defined as a crosslinked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two dimensional surface.) "Gelation time," also referred to herein as "gel time," refers to the time it takes for a composition to become non-flowable under modest stress. This is generally exhibited as reaching a physical state in which the elastic modulus G' equals or exceeds the viscous modulus G", i.e., when tan (delta) becomes 1 (as may be determined using conventional rheological techniques). The gelation time of the present compositions is at most about 1 minute.

The term "adhesive strength" refers to the capability of a composition to remain attached to a surface, e.g., a tissue at the site of administration, when subjected to physical stresses or environmental conditions.

The term "functionalized" refers to a modification of an existing molecular segment to generate or introduce a new reactive functional group (e.g., a maleimido or succinimidyl group) that is capable of undergoing reaction with another functional group (e.g., a sulfhydryl group) to form a covalent bond. For example, a component containing carboxylic acid (—COOH) groups can be functionalized by reaction with N-hydroxy-succinimide or N-hydroxysulfosuccinimide using known procedures, to form a new reactive functional group in the form of an activated carboxylate (which is a reactive electrophilic group), i.e., an N-hydroxysuccinimide ester or an N-hydroxysulfosuccinimide ester, respectively. In another example, carboxylic acid groups can be functionalized by reaction with an acyl halide, e.g., an acyl chloride, again using known procedures, to provide a new reactive functional group in the form of an anhydride.

The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0. Preferred crosslinkable components herein are hydrophilic, although as long as the reactive composition as a whole contains at least one hydrophilic component, crosslinkable hydrophobic components may also be present.

The term "polymer" is used to refer to molecules composed of repeating monomer units, including homopolymers, block copolymers, random copolymers, and graft copolymers. "Polymers" also include linear polymers as well as branched polymers, with branched polymers including highly branched, dendritic, and star polymers. All suitable polymers herein are nontoxic, non-inflammatory and preferably nonimmunogenic, and, ideally, are essentially nondegradable in vivo over a period of at least several months.

The term "polyfunctional," as used to refer to low molecular weight crosslinking agents (i.e., crosslinking agents generally containing up to about 14 carbon atoms), indicate a chemical compound containing two or more functional groups, either sulfhydryl groups or sulfhydryl-reactive groups. Accordingly, it will be appreciated that when the term "polymer" is used, difunctional and polyfunctional small molecules are included. Such moieties include, by way of example, the sulfhydryl reactive compounds disuccinimidyl suberate (DSS), bis (sulfosuccinimidyl) suberate ($BS^3$), dithiobis-(succinimidylpropionate) (DSP), bis(2-succinimidooxy-carbonyloxy)ethyl sulfone (BSOCOES), and 3,3'-dithiobis (sulfo-succinimidylpropionate) (DTSSP), and the di- and polyfunctional sulfhydryl-containing compounds 1,2-ethanedithiol (HS—$CH_2$—$CH_2$—SH), 1,4-butanedithiol (HS—[$CH_2$]$_4$—SH), 1,5-pentanedithiol (HS—[$CH_2$]$_5$—SH), 1,6-hexane dithiol (HS—[$CH_2$]$_6$—SH), 2-(2-mercapto-ethylsulfanyl)-ethanethiol (HS—($CH_2CH_2S$)$_2$H), 2-{2-[2-(2-mercapto-ethylsulfanyl)-ethylsulfanyl]-ethylsulfanyl}-ethanethiol (HS—($CH_2CH_2S$)$_4$H), 2-(bis-mercaptoethylamino)-ethanethiol (N—[$CH_2CH_2SH$]$_3$), 3-[bis-2-mercaptoethyl)-amino]-propane-1-thiol (N—[$CH_2CH_2CH_2SH$]$_3$), 4-[bis-(3-mercaptopropyl)-amino]-butane-1-thiol (N—[$CH_2CH_2CH_2CH_2SH$]$_3$), 2-mercaptomethyl-propane -1,3-dithiol (HC[$CH_2SH$]$_3$), 3-(2-mercaptoethyl)-hexane-1,6-dithiol (HC[$CH_2CH_2SH$]$_3$), 2,2-bis-mercaptomethyl-propane-1,3-dithiol (C[$CH_2SH$]$_4$), 3,3-bis-(2-mercaptoethyl)-pentane-1,5-dithiol (C[$CH_2CH_2SH$]$_4$), 5,5-bis-(4-mercaptobutyl)-nonane-1,9-dithiol (C[$CH_2CH_2CH_2CH_2SH$]$_4$), 8,8-bis-(6-mercaptohexyl)-pentadecane-1,5-dithiol (C[($CH_2$)$_6$-SH]$_4$), 2-(2-mercapto-ethoxy)-ethanethiol (HS—($CH_2CH_2O$)H), 2-[(2-mercapto-ethoxy)-ethoxy]-ethanethiol (HS-($CH_2CH_2O$)$_2$H), 2-{2-[2-(2-mercapto-ethoxy)-ethoxy]-ethoxy}-ethanethiol (HS—($CH_2CH_2O$)$_3$H), and 2-(2-{2-[2-(2-mercapto-ethoxy)-ethoxy]-ethoxy}-ethoxy)-ethanethiol (HS—($CH_2CH_2O$)$_4$H). Like the polymers useful herein, all suitable polyfunctional agents herein are nontoxic, non-inflammatory and preferably nonimmunogenic, and, ideally, are essentially nondegradable in vivo over a period of at least several months.

The term "synthetic" to refer to various polymers herein is intended to mean "chemically synthesized." Therefore, a synthetic polymer in the present compositions may have a molecular structure that is identical to a naturally occurring polymer, but the polymer per se, as incorporated in the compositions of the invention, has been chemically synthesized in the laboratory or industrially. "Synthetic" polymers also include semi-synthetic polymers, i.e., naturally occurring polymers, obtained from a natural source, that have been chemically modified in some way. Generally, however, the synthetic polymers herein are purely synthetic, i.e., they are neither semi-synthetic nor have a structure that is identical to that of a naturally occurring polymer.

The term "synthetic hydrophilic polymer" as used herein refers to a synthetic polymer composed of molecular segments that render the polymer as a whole "hydrophilic," as defined above. Preferred polymers are highly pure or are purified to a highly pure state such that the polymer is or is treated to become pharmaceutically pure. Most hydrophilic polymers can be rendered water-soluble by incorporating a sufficient number of oxygen (or less frequently sulfur or nitrogen) atoms available for forming hydrogen bonds in aqueous solutions. Hydrophilic polymers useful herein include, but are not limited to: polyalkylene oxides, particularly polyethylene glycol and copolymers of ethylene oxide (e.g., poly(ethylene oxide)-poly(propylene oxide) copolymers), including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly (hydroxyethylmethacrylate), poly(hydroxyethylacrylate), poly(methylalkylsulfoxide methacrylate), poly (methylalkylsulfoxide acrylate) and copolymers of any of the foregoing with each other and/or with additional acrylate species such as aminoethyl acrylate and mono-2-(acryloxy)-ethyl succinate; polymaleic acid; poly(acrylamides) such as polyacrylamide per se, poly(methacrylamide), poly (dimethylacrylamide), and poly(N-isopropyl-acrylamide); poly(olefinic alcohol)s such as poly(vinyl alcohol); poly(N-vinyl lactams) such as poly(vinyl pyrrolidone) and poly(N-vinyl caprolactam); and copolymers of any of the foregoing polymers with each other and/or with other monomeric species.

Hydrophobic polymers and lower molecular weight hydrophobic compounds can also be used in the reactive compositions of the invention, although at least one component of the reactive composition should be hydrophilic. Generally, any hydrophobic component will be a sulfhydryl-reactive component rather than a sulfhydryl-containing compound. Preferably, hydrophobic components herein have a hydrocarbyl core containing less than about 14 carbon atoms, and are thus polyfunctional "low molecular weight" compounds rather than polymers per se. Hydrophobic components having a higher molecular weight hydrocarbyl core generally have very poor solubility in aqueous solutions and, as such, have very long reaction times when mixed with aqueous solutions of synthetic polymers containing multiple nucleophilic groups.

The term "collagen" as used herein refers to all forms of collagen, including those, which have been processed or otherwise modified. Preferred collagens are treated to remove the immunogenic telopeptide regions ("atelopeptide collagen"), are soluble, and may be in fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may also be used to form particularly rigid crosslinked compositions. Collagen crosslinked using glutaraldehyde or other (nonpolymer) linking agents is typically referred to herein as "GAX" while collagen crosslinked using heat and/or radiation is termed "HRX." Collagen used in connection with the preferred embodiments of the invention is in a pharmaceutically pure form such that it can be incorporated into a human body for the intended purpose.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "effective amount" refers to the amount of composition required in order to obtain the effect desired. Thus, a "tissue growth-promoting amount" of a composition refers to the amount needed in order to stimulate tissue growth to a detectable degree. Tissue, in this context, includes connective tissue, bone, cartilage, epidermis and dermis, blood, and other tissues. The actual amount that is determined to be an effective amount will vary depending on factors such as the size, condition, sex and age of the patient and can be more readily determined by the caregiver.

The term "solid implant" refers to any solid object which is designed for insertion and use within the body, and includes bone and cartilage implants (e.g., artificial joints, retaining pins, cranial plates, and the like, of metal, plastic and/or other materials), breast implants (e.g., silicone gel envelopes, foam forms, and the like), catheters and cannulas intended for long-term use (beyond about three days) in place, artificial organs and vessels (e.g., artificial hearts, pancreases, kidneys, blood vessels, and the like), drug delivery devices (including monolithic implants, pumps and controlled release devices such as Alzet® minipumps, steroid pellets for anabolic growth or contraception, and the like), sutures for dermal or internal use, periodontal membranes, ophthalmic shields, corneal lenticules, and the like.

The term "suitable fibrous material" as used herein, refers to a fibrous material which is substantially insoluble in water, non-immunogenic, biocompatible, and immiscible with the reactive compositions of the invention. The fibrous material may comprise any of a variety of materials having these characteristics and may be combined with reactive compositions herein in order to form and/or provide structural integrity to various implants or devices used in connection with medical and pharmaceutical uses. For example, the reactive compositions of the invention can be coated on the "suitable fibrous material," which can then be wrapped around a bone to provide structural integrity to the bone. Thus, the "suitable fibrous material" is useful in forming the "solid implants" of the invention.

The term "in situ" as used herein means at the site of administration. Thus, the injectable reaction mixture compositions are injected or otherwise applied to a specific site within a patient's body, e.g., a site in need of augmentation, and allowed to crosslink at the site of injection. Suitable sites will generally be intradermal or subcutaneous regions for augmenting dermal support, at a bone fracture site for bone repair, within sphincter tissue for sphincter augmentation (e.g., for restoration of continence), within a wound or suture, to promote tissue regrowth; and within or adjacent to vessel anastomoses, to promote vessel regrowth.

The term "aqueous medium" includes solutions, suspensions, dispersions, colloids, and the like containing water.

The term "substantially immediately" means within less than five minutes, preferably within less than two minutes, and the term "immediately" means within less than one minute, preferably within less than 30 seconds.

The terms "active agent," and "biologically active agent" are used interchangeably herein to refer a chemical compound that induces a desired pharmacological, physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, it is to be understood that applicants intend to include the active agent per se as well as pharmaceutically acceptable, pharmacologically active salts, esters, amides, prodrugs, metabolites, analogs, etc.

The term "gel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry gels swell to the extent allowed by the degree of cross-linking.

With regard to nomenclature pertinent to molecular structures, the following definitions apply:

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups. "Alkylene," "lower alkylene" and "substituted alkylene" refer to divalent alkyl, lower alkyl, and substituted alkyl groups, respectively.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. The terms "arylene" and "substituted arylene" refer to divalent aryl and substituted aryl groups as just defined.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. If not otherwise indicated, "hydrocarbyl" indicates unsubstituted hydrocarbyl, substituted hydrocarbyl, heteroatom-containing hydrocarbyl, and substituted heteroatom-containing hydrocarbyl. Unless otherwise indicated, the terms "hydrocarbyl" and "hydrocarbylene" include substituted hydrocarbyl and substituted hydrocarbylene, heteroatom-containing hydrocarbyl and heteroatom-containing hydrocarbylene, and substituted heteroatom-containing hydrocarbyl and substituted heteroatom-containing hydrocarbylene, respectively.

By "substituted" as in "substituted hydrocarbyl," "substituted alkyl," and the like, as alluded to in some of the aforementioned definitions, is meant that in the hydrocarbyl, alkyl, or other moiety, at least one hydrogen atom bound to a carbon atom is replaced with one or more substituents that are functional groups such as alkoxy, hydroxy, halo, nitro, and the like. Unless otherwise indicated, it is to be understood that specified molecular segments can be substituted with one or more substituents that do not compromise a compound's utility. For example, "succinimidyl" is intended to include unsubstituted succinimidyl as well as sulfosuccinimidyl and other succinimidyl groups substituted on a ring carbon atom, e.g., with alkoxy substituents, polyether substituents, or the like.

In accordance with the present invention, then, a reactive composition is provided that contains at least one sulfhydryl-containing component and at least one sulfhydryl-reactive component. The invention also encompasses reactive systems in which the sulfhydryl-containing component(s) and the sulfhydryl-reactive component(s) are maintained separately, rather than in an admixture. Upon admixture, however, and under suitable reaction conditions, the sulfhydryl-containing component and the sulfhydryl-reactive component rapidly react to form a crosslinked gel.

When the sulfhydryl-reactive component is an electrophile, such that the rapid gelation reaction involves nucleophilic attack by the sulfhydryl groups, suitable reaction conditions will involve:

(1) simple admixture of the components, without an added solvent, provided that at least one of the components is a liquid and thus serves as a solvent as well as a reactant (Method A);

(2) Method A plus an added base, if the components are otherwise insufficiently reactive with each other to form a crosslinked gel substantially immediately upon admixture, preferably in less than one minute, more preferably in less than 30 seconds, optimally in less than 15 seconds (Method B);

(3) admixture of the components in a polar solvent, preferably an aqueous medium (Method C); or (4) Method C plus an added base, if the components are otherwise insufficiently reactive with each other to form a crosslinked gel substantially immediately upon admixture in the solvent (method D).

Methods A and B require that one of the components be a liquid, so as to serve as a solvent for the crosslinking reaction as well as a reactive component. Methods C and D must be used when none of the components is a liquid that could serve as a reaction solvent, and may optionally be used when one of the components is such a liquid.

When the sulfhydryl-reactive component is one that reacts with a sulfhydryl group via a free radical mechanism, suitable reaction conditions will involve:

(5) crosslinking in bulk (wherein, as in Methods A and B, at least one of the components must be a liquid at ambient temperature), by admixing the components with a free radical initiator and irradiating the reaction mixture (Method E) or (6) admixing the components in a solvent, along with a free radical initiator, and irradiating the reaction mixture as in Method E (Method F).

The components of the reactive composition are selected so that crosslinking gives rise to a biocompatible gel matrix useful in a variety of contexts, including adhesion, biologically active agent delivery, tissue augmentation, and other applications.

II. The Components of the Reactive Composition

The reactive composition of the invention is comprised of at least two crosslinkable components: a first component, component A, which has m sulfhydryl groups, wherein $m \geq 2$; and a second component, component B, which has n sulfhydryl-reactive groups capable of reaction with the m sulfhydryl groups. The composition may include additional sulfhydryl-containing components and/or sulfhydryl-reactive components, wherein any such additional component also contains two or more sulfhydryl or sulfhydryl-reactive groups. Preferably, m+n>4, to ensure formation of a sufficiently three-dimensional crosslinked matrix. More preferably, at least one of m and n is $\geq 3$, and most preferably, m and n are each $\geq 4$; for example, m and n may both be 4, or one of m and n is 4 and the other is 8. Increasing m and n in turn increases the rate at which the three-dimensional polymeric gel is formed. For extremely fast-reacting compositions, and/or when increased compressive strength is necessary, m and n are each $\geq 12$. Each of the components is biocompatible, and at least one component is comprised of a hydrophilic polymer.

The components may be represented by the structural formulae $$R^1(-[Q^1]_q-SH)_m \qquad (I)$$

(component A), and $$R^2(-[Q^2]_r-Y)_n \qquad (II)$$

(component B), wherein:

$R^1$ and $R^2$ are independently selected from the group consisting of $C_2$ to $C_{14}$ hydrocarbyl, heteroatom-containing $C_2$ to $C_{14}$ hydrocarbyl, hydrophilic polymers, and hydrophobic polymers, providing that at least one of $R^1$ and $R^2$ is a hydrophilic polymer, preferably a synthetic hydrophilic polymer;

Y represents one of the n sulfhydryl-reactive groups of component B, and the various Y moieties on B may be the same or different;

$Q^1$ and $Q^2$ are linking groups; and $m \geq 2$, $n \geq 2$, the sum of m+n is preferably >4, and q and r are independently zero or 1.

A. Reactive Groups

The sulfhydryl group on component A may be bound directly or indirectly to a polymer core or to the core of a low molecular weight reactive component, as noted above. The sulfhydryl-reactive group is selected so that crosslinking and gelation occur rapidly upon admixture of the sulfhydryl-containing component with the sulfhydryl-reactive component. Therefore, sulfhydryl-reactive group Y can be one of any number of electrophilic groups, so long as reaction can take place with a sulfhydryl moiety. The only limitation is a practical one, in that reaction between the components should take place without need for heat or potentially toxic or non-biodegradable reaction catalysts or other chemical reagents. Ideally, the reactions between the sulfhydryl-containing component and the sulfhydryl-reactive component should be complete in under one minute, preferably in under 30 seconds, most preferably in under 15 seconds.

The linkage —Z— formed upon reaction of the sulfhydryl-containing component A with the sulfhydryl-reactive component B

may be a thioester, a thioether, a disulfide, or the like. A wide variety of sulfhydryl-reactive groups and the types of linkages they form when reacted with sulfhydryl groups are well known in the scientific literature. See, for example, Bodanszky, M., *Principles of Peptide Synthesis*, 2nd ed., pages 21 to 37, Springer-Verlag, Berlin (1993); and Lundbland, R. L., *Chemical Reagents for Protein Modification*, 2nd ed., Chapter 6, CRC Press, Boca Raton, Fla. (1991).

Examples of sulfhydryl-reactive components that form thioester linkages with sulfhydryl groups in a nucleophilic substitution reaction, i.e., wherein the sulfhydryl group acts as a nucleophile, are depicted in FIG. 1 and include, inter alia, the following compounds, with the numbers in parentheses corresponding to the structures shown in FIG. 1:

anhydrides, including mixed anhydrides such as PEG-glutaryl-acetyl-anhydride (1), PEG-glutaryl-isovaleryl-anhydride (2), PEG-glutaryl-pivaloyl-anhydride (3) and related compounds as described by Bodanszky, supra, at p. 23;

esters, including ester derivatives of phosphorus, such as structures (4) and (5), ester derivatives of p-nitrophenol (6) of p-nitrothiophenol (7), of pentafluorophenol (8), of structure (9), related active esters as presented by Bodanszky (pp. 31–32, and Table 2), esters of substituted hydroxylamines, such as those of N-hydroxy-phthalimide (10), N-hydroxy-succinimide (11), and N-hydroxy-glutarimide (12), N-hydroxysulfosuccinimide esters and related structures in Bodanszky, Table 3, and esters of 1-hydroxybenzotriazole (13), 3-hydroxy-3,4-dihydro-benzotriazine-4-one (14) and 3-hydroxy-3,4-dihydro-quinazoline-4-one, carbonylimidazole derivatives;

acid chlorides;

ketenes; and isocyanates.

With these compounds, auxiliary reagents can also be used to facilitate bond formation, e.g., 1-ethyl-3-[3-dimethylaminopropyl]carbodiimide can be used to facilitate coupling of sulfhydryl groups to carboxyl-containing groups. Additionally, reaction can be carried out in the presence of a base, so as to increase the rate of the crosslinking reaction.

In addition to the sulfhydryl reactive groups that form thioester linkages, various other sulfhydryl reactive functionalities can be utilized that form other types of linkages. For example, compounds that contain methyl imidate derivatives form imido-thioester linkages with sulfhydryl groups. Alternatively, sulfhydryl-reactive groups can be employed that form disulfide bonds with sulfhydryl groups; in one example, such groups have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridyl, o-nitrophenyl, m-nitrophenyl, p-nitrophenyl, 2,4-dinitrophenyl, 2-nitro-4-benzoic acid, 2-nitro-4-pyridyl, etc. Specific examples of sulfhydryl-reactive components that form disulfide bonds upon reaction with a sulfhydryl group include o-pyridyl disulfide, 3-nitro-2-pyridinesulfenyl, 2-nitro-5-thiocyanato-benzoic acid, 5,5'-dithio-bis(2-nitrobenzoic acid), methane thiosulfate derivatives, and 2,4-dinitrophenyl cysteinyl disulfide. In such instances, auxiliary reagents, i.e., mild oxidizing agents such as hydrogen peroxide, can be used to facilitate disulfide bond formation.

Yet another class of sulfhydryl-reactive groups forms thioether bonds with sulfhydryl groups. Such groups include, inter alia, unsaturated functionalities, i.e., groups containing one or more unsaturated bonds, as well as haloalkyl, haloaryl, epoxy, imino, and aziridino groups. When the sulhydryl-reactive group is an unsaturated functionality, such that the sulfhydryl group adds to an unsaturated bond, reaction may be by a nucleophilic, electrophilic, or free radical mechanism, although nucleophilic and free radical reactions are preferred for rapid reaction. Nucleophilic reaction will proceed with those unsaturated functionalities that are alkynes, contain conjugated double bonds, and/or that act as Michael-type substrates, with the latter typically referring to groups that contain the moiety —C=C—Z where Z is an electron-withdrawing moiety such as a carbonyl group, halo or nitro; as such, adding a base to the reaction mixture will increase the rate of reaction and is thus carried out in a preferred embodiment. Examples of unsaturated sulfhydryl-reactive groups that will undergo reaction with thiols via a nucleophilic mechanism thus include, but are not limited to, maleimido, substituted maleimido (e.g., ethyl maleimido, dextran maleimido, etc.), ethyleneimino, acrylate, methacrylate, and ethenesulfonyl groups, as well as $\alpha,\beta$-unsaturated aldehydes and ketones. For other unsaturated sulfhydryl-reactive groups, reaction with sulfhydryl moieties proceeds via a free radical mechanism, and is thus carried out in the presence of a free radical initiator, preferably in combination with irradiation. These unsaturated sulfhydryl-reactive groups include, by way of example, monounsaturated alkenyl, typically monounsaturated lower alkenyl (including, for example, vinyl and allyl), allyl ether, vinyl ether, imino, and the like.

The covalent linkages in the crosslinked structure that result upon covalent binding of sulfhydryl-containing components to specific sulfhydryl-reactive components in the reactive composition include, solely by way of example, the following (the optional linking groups $Q^1$ and $Q^2$ are omitted for clarity):

B. Linking Groups

The functional groups SH and Y may be directly attached to the component core ($R^1$ or $R^2$, respectively), or they may be indirectly attached through a linking group, with longer linking groups also termed "chain extenders." In structural formulae (I) and (II),

(component A)

(component B) the optional linking groups are represented by $Q^1$ and $Q^2$, wherein the linking groups are present when q and r are equal to 1 (with $R^1$, $R^2$, Y, m and n as defined previously).

Suitable linking groups are well known in the art. Linking groups are useful to avoid steric hindrance problems that are sometimes associated with the formation of direct linkages between molecules. Linking groups may additionally be used to link several multifunctionally activated compounds together to make larger molecules. In a preferred embodiment, a linking group can be used to alter the degradative properties of the compositions after administra-

TABLE 1

| SULFHYDRYL COMPONENT (A) | REPRESENTATIVE SULFHYDRYL-REACTIVE COMPONENT (B) | RESULTING LINKAGE |
|---|---|---|
| $R^1$—SH | $R^2$—O—(CO)—O—N(COCH$_2$) | $R^1$—S—(CO)—O—$R^2$ |
| $R^1$—SH | $R^2$—(CO)—O-(p-nitrobenzyl) | $R^1$—S—(CO)—$R^2$ |
| $R^1$—SH | $R^2$—S—S-(o-pyridyl) | $R^1$—S—S—$R^2$ |
| $R^1$—SH | $R^2$—S—C≡N | $R^1$—S—$R^2$ |
| $R^1$—SH | $R^2$—O—(CO)—CH=CH$_2$ | $R^1$—S—CH$_2$CH$_2$—(CO)—O—$R^2$ |
| $R^1$—SH | $R^2$—CH$_2$—CH$_2$—I | $R^1$—S—CH$_2$CH$_2$—$R^2$ |
| $R^1$—SH | $R^2$—C$_6$H$_4$—F | $R^1$—S—C$_6$H$_4$—$R^2$ |
| $R^1$—SH | $R^2$—O(CO)—(CH$_2$)$_3$—CO$_2$—N(COCH$_2$) | $R^1$—S—(CO)—(CH$_2$)$_3$—(CO)—O$R^2$ |
| $R^1$—SH | $R^2$—O—CH$_2$—CO$_2$—N(COCH$_2$) | $R^1$—S—(CO)—CH$_2$—O$R^2$ |
| $R^1$—SH | $R^2$—O—NH(CO)—(CH$_2$)$_2$—CO$_2$—N(COCH$_2$) | $R^1$—S—(CO)—(CH$_2$)$_2$—(CO)—NH—O$R^2$ |
| $R^1$—SH | $R^2$—SO$_2$—CH=CH$_2$ | $R^1$—S—CH$_2$CH$_2$—SO$_2$—$R^2$ |
| $R^1$—SH | $R^2$—O—CH=CH$_2$ | $R^1$—S—CH$_2$CH$_2$—O—$R^2$ |
| $R^1$—SH | $R^2$—O—CH$_2$—CH=CH$_2$ | $R^1$—S—CH$_2$CH$_2$CH$_2$—O—$R^2$ |

The sulfhydryl-reactive groups may be present on a commercially available compound, or they may be synthetically introduced by chemical modification (also termed "activation") of other types of functional groups present on a compound.

Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form the N-hydroxysuccinimide ester and the N-hydroxysulfosuccinimide ester, respectively, both of which are sulfhydryl-reactive groups. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

tion and resultant gel formation. For example, linking groups can be incorporated into components A and/or B to promote hydrolysis, to discourage hydrolysis, or to provide a site for enzymatic degradation.

Examples of linking groups that provide hydrolyzable sites, include, inter alia: ester linkages; anhydride linkages, such as obtained by incorporation of glutarate and succinate; ortho ester linkages; ortho carbonate linkages such as trimethylene carbonate; amide linkages; phosphoester linkages; α-hydroxy acid linkages, such as may be obtained by incorporation of lactic acid and glycolic acid; lactone-based linkages, such as may be obtained by incorporation of caprolactone, valerolactone, γ-butyrolactone and p-dioxanone; and amide linkages such as in a dimeric, oligomeric, or poly(amino acid) segment. Examples of non-degradable linking groups include succinimide, propionic acid and carboxymethylate linkages. See, for example, PCT WO 99/07417. Examples of enzymatically degradable linkages include Leu—Gly—Pro—Ala, which is degraded by collagenase; and Gly—Pro—Lys, which is degraded by plasmin.

Linking groups can also enhance or suppress the reactivity of the sulfhydryl and sulfhydryl-reactive groups. For example, electron-withdrawing groups within one or two carbons of a sulfhydryl group would be expected to diminish its effectiveness in coupling, due to a lowering of nucleophilicity. Carbon-carbon double bonds and carbonyl groups will also have such an effect. Conversely, electron-withdrawing groups adjacent to a sulfhydryl-reactive carbonyl group (e.g., the reactive carbonyl of glutaryl-N-hydroxysuccinimidyl) would increase the reactivity of the carbonyl carbon with respect to an incoming nucleophilic thiol. By contrast, sterically bulky groups in the vicinity of a functional group can be used to diminish reactivity and thus coupling rate as a result of steric hindrance.

By way of example, particular linking groups and corresponding component structure are indicated in Table 2:

TABLE 2

| LINKING GROUP | COMPONENT STRUCTURE |
|---|---|
| —O—$(CH_2)_n$— | Component A: $R^1$—O—$(CH_2)_n$—SH |
| | Component B: $R^2$—O—$(CH_2)_n$—Y |
| —S—$(CH_2)_n$— | Component A: $R^1$—S—$(CH_2)_n$—SH |
| | Component B: $R^2$—S—$(CH_2)_n$—Y |
| —NH—$(CH_2)_n$— | Component A: $R^1$—NH—$(CH_2)_n$—SH |
| | Component B: $R^2$—NH—$(CH_2)_n$—Y |
| —O—(CO)—NH—$(CH_2)_n$— | Component A: $R^1$—O—(CO)—NH—$(CH_2)_n$—SH |
| | Component B: $R^2$—O—(CO)—NH—$(CH_2)_n$—Y |
| —NH—(CO)—O—$(CH_2)_n$— | Component A: $R^1$—NH—(CO)—O—$(CH_2)_n$—SH |
| | Component B: $R^2$—NH—(CO)—O—$(CH_2)_n$—Y |
| —O—(CO)—$(CH_2)_n$— | Component A: $R^1$—O—(CO)—$(CH_2)_n$—SH |
| | Component B: $R^2$—O—(CO)—$(CH_2)_n$—Y |
| —(CO)—O—$(CH_2)_n$— | Component A: $R^1$—(CO)—O—$(CH_2)_n$—SH |
| | Component B: $R^2$—(CO)—O—$(CH_2)_n$—Y |
| —O—(CO)—O—$(CH_2)_n$— | Component A: $R^1$—O—(CO)—O—$(CH_2)_n$—SH |
| | Component B: $R^2$—O—(CO)—O—$(CH_2)_n$—Y |
| —O—(CO)—$CHR^3$— | Component A: |
| | $R^1$—O—(CO)—$CHR^3$—SH |
| | Component B: $R^2$—O—(CO)—$CHR^3$—Y |
| —O—$R^4$—(CO)—NH— | Component A: |
| | $R^1$—O—$R^4$—(CO)—NH—SH |
| | Component B: $R^2$—O—$R^4$—(CO)—NH—Y |

In the table, "n" is generally in the range of 1 to about 10, $R^4$ is generally hydrocarbyl, typically alkyl or aryl, preferably alkyl, and most preferably lower alkyl, and $R^5$ is hydrocarbylene, heteroatom-containing hydrocarbylene, substituted hydrocarbylene, or substituted heteroatom-containing hydrocarbylene) typically alkylene or arylene (again, optionally substituted and/or containing a heteroatom), preferably lower alkylene (e.g., methylene, ethylene, n-propylene, n-butylene, etc.), phenylene, or amidoalkylene (e.g., —(CO)—NH—$CH_2$).

Other general principles that should be considered with respect to linking groups are as follows: If higher molecular weight components are to be used, they preferably have biodegradable linkages as described above, so that fragments larger than 20,000 mol. wt. are not generated during resorption in the body. In addition, to promote water miscibility and/or solubility, it may be desired to add sufficient electric charge or hydrophilicity.

C. The Component Core

The "core" of each reactive component is comprised of the molecular structure to which the sulfhydryl or sulfhydryl-reactive groups are bound. Using the formulae (I) $R^1$—$[Q^1]_q$—$X)_m$, for component A and (II) $R^2$(—$[Q^2]_r$— $Y)_n$ for component B, the "core" groups are $R^1$, $R^2$ and $R^3$. Each molecular core of the reactive components is generally selected from synthetic and naturally occurring hydrophilic polymers, hydrophobic polymers, and $C_2$–$C_{14}$ hydrocarbyl groups containing zero to 2 heteroatoms selected from N, O and S. Generally, and preferably, at least one of components A and B comprises a molecular core of a hydrophilic polymer. In a preferred embodiment, at least two of A and B comprise a molecular core of a hydrophilic polymer.

1. Hydrophilic Polymers and "Activation" Thereof

A "hydrophilic polymer" as used herein refers to a polymer having an average molecular weight and composition effective to render the polymer "hydrophilic" as defined in Part (I) of this section. The polymer may be synthetic, semi-synthetic, or naturally occurring.

Synthetic hydrophilic polymers useful herein include, but are not limited to: polyalkylene oxides, particularly polyethylene glycol and copolymers of ethylene oxide (e.g., poly(ethylene oxide)-poly(propylene oxide)copolymers), including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; poly (oxyalkylene)-substituted saccharides such as polyoxyethylated sorbitol and polyoxyethylated glucose; acrylate-based polymers, i.e., acrylic acid and acrylic ester polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate)s, poly(methylalkylsulfoxide acrylate)s and copolymers of any of the foregoing with each other and/or with additional acrylate species such as aminoethyl acrylate and mono-2-(acryloxy)-ethyl succinate; polymaleic acid; poly(acrylamide)s such as polyacrylamide per se, poly (methacrylamide), poly(dimethylacrylamide), and poly(N-isopropyl-acrylamide); poly(olefinic alcohol)s such as poly (vinyl alcohol); poly(N-vinyl lactam)s such as poly(vinyl pyrrolidone) and poly(N-vinyl caprolactam); and copolymers of any of the foregoing polymers with each other and/or with other monomeric species.

It must be emphasized that the aforementioned list of polymers is not exhaustive, and that a variety of other synthetic hydrophilic polymers may be advantageously used in the practice of the invention.

The synthetic hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like.

Other suitable synthetic hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly(lysine)s for use in the present invention preferably have a molecular weight within the range of about 1,000 to about 300,000, more preferably within the range of about 5,000 to about 100,000, and most preferably, within the range of about 8,000 to about 15,000. Poly(lysine)s of varying molecular weights are commercially available from Peninsula Laboratories, Inc. (Belmont, Calif.).

Although a variety of different synthetic hydrophilic polymers can be used in the present compositions, as indicated above, preferred synthetic hydrophilic polymers are polyethylene glycol (PEG) and polyglycerol (PG), particularly highly branched polyglycerol. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred synthetic hydrophilic polymer for certain applications is a polyethylene glycol (PEG) having a molecular weight within the range of about 100 to about 100,000 mol. wt., although for highly branched PEG, far higher molecular weight polymers can be employed—up to 1,000,000 or more—providing that biodegradable sites are incorporated ensuring that all degradation products will have a molecular weight of less than about 30,000. For most PEGs, however, the preferred molecular weight is about 1,000 to about 20,000 mol. wt. Most preferably, the polyethylene glycol has a molecular weight of approximately 10,000 mol. wt.

Naturally occurring hydrophilic polymers include, but are not limited to: proteins such as collagen, fibronectin, albumins, globulins, fibrinogen, fibrin and thrombin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

In general, collagen from any source may be used in the compositions of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. Commonly owned U.S. Pat. No. 5,428,022, issued Jun. 27, 1995 to Palefsky et al., discloses methods of extracting and purifying collagen from the human placenta. Commonly owned U.S. Pat. No. 5,667,839, issued Sep. 16, 1997 to Berg, discloses methods of producing recombinant human collagen in the milk of transgenic animals, including transgenic cows. The term "collagen" or "collagen material" as used herein refers to all forms of collagen, including those that have been processed or otherwise modified.

Collagen of any type, including, but not limited to, types I, II, III, IV, or any combination thereof, may be used in the compositions of the invention, although type I is generally preferred. Either atelopeptide or telopeptide-containing collagen may be used; however, when collagen from a source, such as bovine collagen, is used, atelopeptide collagen is generally preferred, because of its reduced immunogenicity compared to telopeptide-containing collagen. Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from Cohesion Corporation (Palo Alto, Calif.) at collagen concentrations of 35 mg/ml and 65 mg/ml under the trademarks Zyderm® I Collagen and Zyderm® II Collagen, respectively. Glutaraldehyde-crosslinked atelopeptide fibrillar collagen is commercially available from Cohesion Corporation at a collagen concentration of 35 mg/ml under the trademark Zyplast®. Collagens for use in the present invention are generally, although not necessarily, in aqueous suspension at a concentration between about 20 mg/mil to about 120 mg/ml, preferably between about 30 mg/ml to about 90 mg/ml.

Although intact collagen is preferred, denatured collagen, commonly known as gelatin, can also be used in the compositions of the invention. Gelatin may have the added benefit of being degradable faster than collagen. Because of its tacky consistency, nonfibrillar collagen is generally preferred for use in compositions of the invention that are intended for use as bioadhesives. The term "nonfibrillar collagen" refers to any modified or unmodified collagen material that is in substantially nonfibrillar form at pH 7, as indicated by optical clarity of an aqueous suspension of the collagen. Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII. Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Due to its inherent tackiness, methylated collagen is particularly preferred for use in bioadhesive compositions, as disclosed in commonly owned U.S. Pat. No. 5,614,587 to Rhee et al.

Collagens for use in the reactive compositions of the present invention may start out in fibrillar form, then rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo. Because it is opaque and less tacky than nonfibrillar collagen, fibrillar collagen is less preferred for use in bioadhesive compositions. However, as disclosed in commonly owned, U.S. application Ser. No. 08/476,825, fibrillar collagen, or mixtures of nonfibrillar and fibrillar collagen, may be preferred for use in adhesive compositions intended for long-term persistence in vivo, if optical clarity is not a requirement. For those compositions intended to be used in tissue augmentation, fibrillar collagen is preferred because it tends to form stronger crosslinked gels having greater long-term persistency in vivo than those prepared using nonfibrillar collagen.

Any of the hydrophilic polymers herein must contain, or be modified or functionalized to contain, functional groups, i.e., sulfhydryl groups or sulfhydryl-reactive groups. "Activation" of PEG, i.e., modification or functionalization of PEG to provide selected groups, is discussed below; it is to be understood, however, that the following discussion is for purposes of illustration and analogous techniques may be employed with other polymers.

With respect to PEG, first of all, various functionalized polyethylene glycols have been used effectively in fields such as protein modification (see Abuchowski et al., Enzymes as Drugs, John Wiley & Sons: New York, N.Y. (1981) pp. 367–383; and Dreborg et al., Crit. Rev. Therap. Drug Carrier Syst. (1990) 6:315), peptide chemistry (see Mutter et al., The Peptides, Academic: New York, N.Y. 2:285–332; and Zalipsky et al., Int. J. Peptide Protein Res. (1987) 30:740), and the synthesis of polymeric drugs (see Zalipsky et al., Eur. Polym. J. (1983) 19:1177; and Ouchi et al., J. Macromol. Sci. Chem. (1987) A24: 1011). Activated forms of PEG, including multifunctionally activated PEG, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992); and Shearwater Polymers, Inc. Catalog, Polyethylene Glycol Derivatives, Huntsville, Ala. (1997–1998).

Examples of suitable functionally activated forms of PEG include, without limitation, PEG succinimidyl glutarate, PEG succinimidyl propionate ("SE-PEG"), PEG succinimidyl butylate, PEG succinimidyl acetate, PEG succinimidyl succinamide (SSA-PEG), PEG succinimidyl carbonate (SC-PEG), PEG propionaldehyde (A-PEG), PEG glycidyl ether (E-PEG), PEG-isocyanate (I-PEG), PEG-vinylsulfone (V-PEG), PEG diacrylate ($CH_2$=CH—(CO)—O—PEG—O—(CO)—CH=$CH_2$), PEG di(vinyl ether) ($CH_2$=CH—O—PEG—O—CH=$CH_2$), and PEG di(allyl ether) ($CH_2$=CH—$CH_2$—O—PEG—O—$CH_2$—CH=$CH_2$). For use as a tissue sealant, the preferred combination of activated polymers is as follows: the sulfhydryl-reactive component is the tetrafunctional PEG pentaerythritol poly (ethylene glycol) ether tetra-succinimidyl glutarate (with a preferred molecular weight in the range of about 5000 to 20,000, optimally about 10,000); and the sulfhydryl-containing component is the tetrafunctional PEG pentaerythritol poly(ethylene glycol) ether tetra-sulfhydryl (again, with a preferred molecular weight in the range of about 5000 to 20,000, optimally about 10,000). In both cases, these "four-arm" PEGs are formed by ethoxylation of pentaerythritol (wherein, in a particularly preferred example, each of the four chains has a molecular weight of approximately 2,500) and then derivatized to introduce the functional groups onto each of the four arms. Also preferred are analogous poly(ethylene glycol)-like compounds polymerized from di-glycerol instead of pentaerythritol.

2. Hydrophobic Polymers

The reactive compositions of the invention can also include hydrophobic polymers, although for most uses hydrophilic polymers are preferred. When crosslinking is carried out in bulk, virtually any hydrophobic polymer may be used, unless the gel prepared is a hydrogel, in which case the hydrophobic polymer is preferably a soluble or micelle-forming block copolymer. When crosslinking is carried out in a solvent, polylactic acid, polyglycolic acid, and copolymers of lactic and glycolic acids are representative examples of suitable hydrophobic polymers that can be used. With other hydrophobic polymers, only short-chain oligomers (containing at most about 14 carbon atoms) should be used if crosslinking is carried out in a solvent, to avoid solubility-related problems during reaction.

3. Low Molecular Weight Components

As indicated above, the molecular core of one or two of the reactive components can also be a low molecular weight compound, i.e., a $C_2$–$C_{14}$ hydrocarbyl group containing zero to 2 heteroatoms selected from N, O, S and combinations thereof. Such a molecular core will normally be substituted with sulfhydryl-reactive groups rather than with free sulfhydryl groups.

Figure 2:
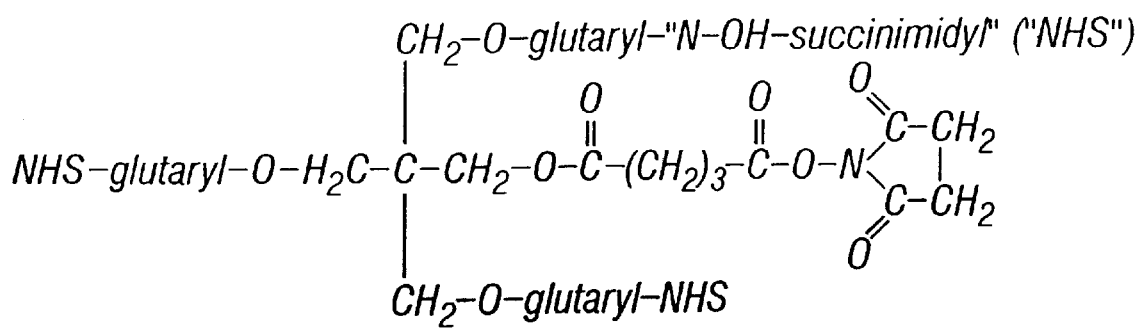
FIG. 2 depicts the structure of a polyfunctional, low molecular weight sulfhydryl-reactive compound.

Such compounds include the di-functional di-succinimidyl esters and di-maleimidyl compounds, as well as other well known commercially available compounds. Examples of such compounds include, by way of example, disuccinimidyl suberate (DSS), bis(sulfosuccinimidyl) suberate ($BS_3$), dithiobis(succinimidylpropionate) (DSP), bis(2-succinimidooxycarbonyloxy)ethyl sulfone (BSOCOES), 3,3'-dithiobis(sulfo-succinimidylpropionate (DTSPP), and their analogs and derivatives. The aforementioned compounds are commercially available from Pierce (Rockford, Ill.). In addition, one of skill in the art can readily synthesize a low molecular weight multi-functional reactive compound using routine organic chemistry techniques. One such compound is shown in FIG. 2, which is a penta-erythritol coupled to four glutarate moieties, with each arm capped with an N-hydroxy-succinimidyl ester (NHS). Analogous compounds can be synthesized from inositol (radiating 6-arm), lactitol (9-arm) or sorbitol (linear 6-arm). The end-capped reactive group can just as easily be sulfhydryl, maleimidyl, vinyl-sulfone, acrylate, vinyl ether, allyl ether, etc., instead of NHS. The polymer or the small molecule can carry either reactive end group as long as there are reactive pairs in the composition such as NHS and SH, maleimidyl and SH, etc.

Low molecular weight, polyfunctional sulfhydryl-reactive components can also be synthesized from diols and polyols using conventional techniques. Diols and polyols that can serve as starting materials here include, without limitation, trimethylolpropane (TMP), di(trimethylol propane) (di-TMP), pentaerythritol, dipentaerythritol (DPE), diglycerol, and oligoglycerol (containing 3–12, preferably 3–10 glycerol units). By way of example, a polyol $R(OH)_n$ may be converted to a poly(allyl ether) $R(-OCH_2-CH=CH_2)_n$ by reaction with 3-chloropropene in the presence of a base. As another example, a polyol $R(OH)_n$ may be converted to a polyacrylate $R(-O-(CO)-CH=CH_2)_n$ by reaction with acryloyl chloride. Other starting materials, co-reactants and synthetic techniques, as well known in the art, may also be used to prepare the components of the invention.

D. Free Radical Initiators

When the sulfhydryl component and the sulfhydryl-reactive component are selected to crosslink via a free radical mechanism, a free radical initiator may be admixed with the components prior to crosslinking. Suitable free radical initiators include any of the conventionally used free radical initiators, e.g., organic peroxides and azo compounds. Organic peroxides useful as free radical initiators include, without limitation, dialkyl peroxides such as t-butyl peroxide and 2,2bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo initiators include, by way of example, azo bis (isobutyronitrile) and azo bis(2,4-dimethylvaleronitrile).

Preferably, crosslinking via a free radical reaction is carried out with radiation, typically in the presence of a "photoinitator," i.e., a free radical initiator that works in conjunction with irradiation of the reaction system, typically with ultraviolet light. Useful photoinitiators include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylacetophenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxycarbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides. Generally, any free radical initiator used represents less than 5 wt. % of the reactive composition, preferably less than 2 wt. % of the composition, most preferably less than 1 wt. % of the composition.

Examples of suitable commercially available initiators include, without limitation, Irgacure® 184, 369, 500, 651, 784, 819, 819XF, 907, 1300, 2020, and 2959 (available from Ciba), Darocur® 1173 and 4265 (also available from Ciba), and Lucirin® TPO, Lucirin® TPO-L, and Lucirin® LR 8953 (available from BASF).

E. Other Components of the Reactive Composition

In addition to the reactive components, the compositions of the present invention may also contain other components. In one embodiment, these additional components are covalently incorporated into the matrix itself by becoming crosslinked to one or both of the reactive components after they are mixed together. In another embodiment, such as would be the case if an additional component were unreactive with either of the reactive components, the additional component becomes physically or ionically associated with the matrix-forming components after mixing, and thus becomes part of the gel matrix itself.

In order to enhance gel strength, it may be generally desirable to add a "tensile strength enhancer" to the composition. Such tensile strength enhancers include, but are not limited to, micron-size high tensile strength fibers, preferably in the range of about 5 to 40 microns in diameter and 20 to 5000 microns in length, and usually with glass transition temperatures or crystalline melting points well above 37° C.

Suitable tensile strength enhancers for use in the present invention include, inter alia, collagen fibers, polyglycolide and polylactide fibers, as well as other organic tensile strength enhancers and inorganic tensile strength enhancers, preferably in fibrous form. A particularly useful tensile strength enhancer is Vicryl® (polyglycolide:polylactide, 90:10) The use of tensile strength enhancers, which are part of the broader category of "fillers," are well known. For example, silicone gums, when cross-linked with peroxides, are weak gels a with tensile strength on the order of only about 34 $N/cm^2$. When suitably compounded with reinforcing fillers, the tensile strength of these gums may increase as much as fifty-fold. Lichtenwalner, H. K. and Sprung, M. N., in Mark, H. F., Gaylord, N. G., and Bikales, N. M., Eds., Encyclopedia of Polymer Science and Technology, Vol. 12, p. 535, John Wiley, New York, 1970. Suitable tensile strength enhancers are those that have inherent high tensile strength and also can interact by covalent or non-covalent bonds with the polymerized gel network. The tensile strength enhancer should bond to the gel, either mechanically or covalently, in order to provide tensile support. Tensile strengths of polyglycolide resorbable sutures are approximately 89,000 $N/cm^2$; that of collagen fibers is 5000–10,000 $N/cm^2$ (Hayashi, T., in Biomedical Applic. of Polym. Mater., Tsuruta, T. et al., Eds., CRC Press, Boca Raton, Fla., 1993).

The reactive compositions can also be prepared to contain various imaging agents such as iodine or barium sulfate, or fluorine, in order to aid visualization of the compositions after administration via x-ray or $^{19}$F-MRI, respectively.

Other naturally occurring polymers may also be incorporated into the compositions; see part (C)(1) of this section. However, it should be emphasized that those naturally occurring polymers will not become covalently incorporated into the composition unless they contain sulfhydryl-reactive groups or nucleophilic groups, thus facilitating reaction with sulfhydryl groups and sulfhydryl-reactive groups, respectively. Proteins, and collagen, in particular, may improve the biocompatibility of the gel, including the potential colonization by cells, promotion of wound healing, etc. Collagen and any amino group-containing proteins would also contribute to the structural integrity of the matrix by becoming covalently bound thereto along with the other gel components. In particular, if PEG-succinimidyl esters are used, the amide bonds formed with collagen will be more stable to hydrolytic degradation than the bonds formed by the reaction of succinimidyl esters with thiol groups. Suitable proteins include, inter alia, collagen, fibronectin, gelatin and albumin, as well as peptide fragments thereof Particularly preferred is collagen, which may be in the form of afibrillar, microfibrillar or fibrillar collagen. Types I and III collagen isolated from bovine corium or human placenta, or prepared by recombinant DNA methods, are suitable. When adding collagen to the present compositions, it is generally important to adjust the concentration of the various components to avoid precipitation.

For use in tissue adhesion as discussed below, it may also be desirable to incorporate proteins such as albumin, fibrin or fibrinogen into the crosslinked polymer composition to promote cellular adhesion.

In addition, the introduction of hydrocolloids such as carboxymethylcellulose may promote tissue adhesion and/or swellability.

F. Storage and Handling

For those sulfhydryl-reactive components that react with water, which are typically those components that serve as electrophilic substrates in a nucleophilic reaction, the components are generally stored and used in sterile, dry form to prevent hydrolysis. Processes for preparing such compounds in sterile, dry form are set forth in commonly assigned U.S. Pat. No. 5,643,464 to Rhee et al. For example, a dry synthetic polymer may be compression molded into a thin sheet or membrane, which can then be sterilized using gamma or, preferably, electron beam irradiation. The resulting dry membrane or sheet can be cut to the desired size or chopped into smaller size particulates. Those sulfhydryl-reactive components that (1) require a base for reaction with sulfhydryl groups and (2) are not reactive in an acidic medium, may be stored in an aqueous acid.

Components containing multiple sulfhydryl groups are generally not water-reactive and can therefore be stored either dry or in aqueous solution. If all components of the reactive composition are prepared in the form of dry, particulate, solids, the various components may be blended and stored in a single container. Admixture of the components with a solvent, e.g., water, saline, or other aqueous media, should not occur until immediately prior to use.

In an alternative embodiment, both components can be mixed together in a single solvent in which they are both unreactive. For example, sulfhydryl-containing components and electrophilic sulfhydryl-reactive groups may be stored in a low pH buffer. Suitable aqueous buffers include, by way of example, monobasic sodium phosphate/dibasic sodium phosphate, sodium carbonate/sodium bicarbonate, glutamate or acetate, at a pH of about 5 to 6.

III. Crosslinking and Gelation

Any number of techniques may be used to effect the rapid reaction between the sulfhydryl component and the sulfhydryl-reactive component, wherein the reaction is a crosslinking process that provides a gel. Generally, however, reaction conditions are used that promote either: (a) a nucleophilic reaction, wherein a sulfhydryl moiety acts as an attacking nucleophile, reacting with an electrophilic sulfhydryl-reactive group; or (b) a free radical reaction, wherein a sulfhydryl radical —S• is formed that adds to a sulfhydryl-reactive group (in this case, a group that reacts with a sulfhydryl radical) generally comprised of an unsaturated bond, e.g., a monounsaturated alkenyl, typically monounsaturated lower alkenyl group (including, for example, vinyl and allyl), allyl ether, vinyl ether, and imino groups, and the like. Preferably, however, the sulfhydryl-containing component and the sulfhydryl-reactive component are selected such that crosslinking occurs fairly rapidly via a nucleophilic reaction upon admixture of all components of the reactive composition with an aqueous medium in the presence of an added base.

With sulfhydryl-reactive components selected to undergo nucleophilic reaction with sulfhydryl groups, the pH of the aqueous medium in which admixture takes place is not always critical. That is, some particularly reactive sulfhydryl-reactive groups are capable of undergoing rapid reaction with sulfhydryl groups in the absence of an added base. However, for most sulfhydryl-reactive components that undergo nucleophilic reaction with sulfhydryl groups, a basic pH is necessary for rapid reaction to occur. In the latter case, the medium in which crosslinking takes place between the components to form a gel should have a pH greater than 7, preferably in the range about 7.5 to about 11, more preferably in the range of about 8 to about 10.5, and most preferably in the range of about 8.5 to about 10.5. The basic pH is provided by addition of an organic or inorganic base, and/or by inclusion of a buffer system that provides a pH in the desired range.

Preferred bases are inorganic, and include, for example, metal salts of weak acids, inorganic oxides, ammonium hydroxide, and metal hydroxides. More preferred bases are as follows: alkali metal and alkaline earth metal salts of weak acids, including, solely by way of example, sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), ammonium phosphate (dibasic), and the like; the inorganic oxides magnesium oxide and calcium oxide; ammonium hydroxide; and alkali metal hydroxides and alkaline earth metal hydroxides, such as sodium hydroxide, calcium hydroxide, potassium hydroxide, magnesium hydroxide, and the like. Most preferred are alkali metal and alkaline earth metal salts of weak acids.

Preferred buffer systems for maintaining a suitably basic pH have a pK in the range of about 7.5 to 10.5, and are comprised of carbonates, borates, phosphates, or AMPSO (3-[(1,1-dimethyl-2-hydroxyethyl)amino]2-hydroxy-propane-sulfonic acid).

When the sulfhydryl-reactive component requires activation with base for rapid reaction to occur, it is preferred that both reactive components be contained in a single aqueous composition maintained at a pH that is sufficiently low to prevent reaction between the sulfhydryl groups and the sulfhydryl-containing groups. The composition is rendered basic immediately prior to administration to initiate reaction between the components, by addition of a base and/or buffer system as described above. Another alternative is to provide the sulfhydryl-reactive component in an acidic medium, e.g., an aqueous acid having a pH in the range of about 3 to about 6, preferably about 4 to about 6, followed by mixing with a basic aqueous medium containing the sulfhydryl-containing component, wherein the basic aqueous medium is sufficiently basic so as to provide the admixture with a pH in the range of about 7.5 to about 11.

Alternatively, the sulfhydryl-reactive component may be in the form of a solid, dehydrated powder, which is then mixed with the sulfhydryl-containing component and a solvent, preferably an aqueous medium, immediately prior to or upon administration. For certain sulfhydryl-reactive components, as noted above, the aqueous medium must contain a base as noted above.

For components selected to crosslink via a free radical mechanism rather than by nucleophilic substitution, a free radical initiator, as discussed in part (D) of Section II, may be admixed with the reactive components prior to initiate crosslinking. Alternatively, or in addition, the reactive composition, i.e., the admixture of the reactive components, any other components, and the optional free radical initiator, are then irradiated with radiation, preferably ultraviolet radiation having a wavelength of 200 to 800 nm, preferably 200 to 500 nm. Low intensity ultraviolet light is sufficient to induce crosslinking in most cases. Thermally induced radical formation may also be used, but is less preferred.

In general, the combined concentration of all reactive components in the reaction mixture will be in the range of about 0.1 to 100 wt. % (with "100 wt. %" representing crosslinking in bulk, i.e., with no added solvent), generally about 1 to 50 wt. %, most typically about 10 to 40 wt. %. However, a preferred concentration of the reactive composition in the solvent, if one is used—as well as the preferred concentration of each crosslinkable component therein—will depend on a number of factors, including the type of component, its molecular weight, and the end use of the composition. For example, use of higher concentrations of the crosslinkable components, or using highly functionalized components, will result in the formation of a more tightly crosslinked network, producing a stiffer, more robust gel. As such, compositions intended for use in tissue augmentation will generally employ concentrations of crosslinkable components that fall toward the higher end of the preferred concentration range. Compositions intended for use as bioadhesives or in adhesion prevention do not need to be as firm and may therefore contain lower concentrations of the crosslinkable components. The appropriate concentration of each crosslinkable component can easily be optimized to achieve a desired gelation time and gel strength using routine experimentation.

More particularly, if the composition components are each 4-arm PEGs, each contained in an aqueous medium, a concentration of about 10–25 wt. % of each component before mixing results in a PEG—PEG gel, after mixing, with an elastic modulus G' of approximately 5 to 10 N/cm$^2$. Such a composition is suitable for use as a surgical sealant. Using methylated collagen and 4-arm succinimidyl PEG, concentrations of 2–4 wt. % and 0.2–0.4 wt. %, respectively, result in gels with a somewhat higher cohesive strength. Using albumin as one of the components, concentrations of 30 wt. % or more provide a similar cohesive strength. Using the preferred four-arm PEGs described above, the polymeric components are generally present at a concentration of 2 to 50 wt. %, and more preferably 10–25 wt. %.

For those reactive compositions in which one or more of the reactive components is a liquid at ambient temperature, crosslinking may take place in the absence of an added solvent, i.e., in bulk, providing that the sulfhydryl component and the sulfhydryl-reactive component react sufficiently rapidly without an added solvent. When crosslinking is conducted in bulk using components that react via a nucleophilic substitution mechanism, a base may be added to facilitate reaction and decrease gelation time. Typically, components that are liquid at ambient temperature and useful in the aforementioned bulk crosslinking process include low molecular weight PEG structures, having a molecular weight on the order of 1000 or less.

IV. Administration and Use

The compositions of the present invention may be administered before or during the gelation reaction, or may be administered immediately after gelation has begun. Certain uses, which are discussed in greater detail below, such as tissue augmentation, may require the compositions to be gelled before administration, whereas other applications, such as tissue adhesion, require the compositions to be administered before the gel point has been reached.

The compositions of the present invention may be delivered to the site of administration in such a way that the individual components of the composition come into contact with each another for the first time at the site of administration or immediately preceding administration. Thus, the compositions of the present invention may be delivered to the site of administration using an apparatus that allows the components to be delivered separately. Such delivery systems usually involve a multi-compartment spray device, but may also comprise any type of controllable extrusion system; alternatively, the components may be delivered manually in the form of separate pastes, liquids or dry powders, which are mixed together manually at the site of administration. Many devices that are adapted for delivery of multi-component tissue sealants/hemostatic agents are well known in the art and can also be used in the practice of the present invention.

Yet another way of delivering the compositions of the present invention is to prepare the reactive components in inactive form as either a liquid or powder. Such compositions can then be activated after application to the tissue site, or immediately beforehand, by applying an activator. In one embodiment, the activator is a buffer solution having a pH that will activate the composition once mixed therewith. Still another way of delivering the compositions is to prepare preformed sheets, and apply the sheets as such to the site of administration.

The reactive compositions of the present invention can be used in a variety of different applications. In general, the present compositions can be adapted for use in any tissue engineering application where synthetic gel matrices are currently being utilized. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art can easily determine the appropriate administration protocol to use with any particular composition having a known gel strength and gelation time. A more detailed description of several specific applications is given below:

Tissue Sealants and Adhesives

In a preferred application, the compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid. These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material. In addition, the compositions can be used to fill spaces in soft and hard tissues that are created by disease or surgery.

Biologically Active Agent Delivery

The crosslinked compositions of the invention may also be used for localized delivery of various drugs and other biologically active agents. Biologically active agents such as growth factors may be delivered from the composition to a local tissue site in order to facilitate tissue healing and regeneration.

The term "biologically active agent" refers to an organic molecule that exerts biological effects in vivo. Examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

Preferred biologically active agents for use in the compositions of the present invention are cytokines, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example, TGF-.beta.1, TGF-.beta.2, TGF-.beta.3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the crosslinked synthetic polymer composition by admixture. Alternatively, the agents may be incorporated into the crosslinked polymer matrix by binding these agents to the functional groups on the synthetic polymers. Processes for covalently binding biologically active agents such as growth factors using functionally activated polyethylene glycols are described in commonly assigned U.S. Pat. No. 5,162,430, issued Nov. 10, 1992, to Rhee et al. Such compositions preferably include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the crosslinked polymer composition involves mixing the active agent with a polyelectrophilic component prior to addition of the polynucleophilic component.

By varying the relative molar amounts of the different components of the reactive composition, it is possible to alter the net charge of the resulting crosslinked polymer composition, in order to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of a polynucleophilic component is used, the resulting matrix has a net positive charge and can be used to ionically bind and deliver negatively charged compounds. Examples of negatively charged compounds that can be delivered from these matrices include various drugs, cells, proteins, and polysaccharides. Negatively charged collagens, such as succinylated collagen, and glycosaminoglycan derivatives such as sodium hyaluronate, keratan sulfate, keratosulfate, sodium chondroitin sulfate A, sodium dermatan sulfate B, sodium chondroitin sulfate C, heparin, esterified chondroitin sulfate C, and esterified heparin, can be effectively incorporated into the crosslinked polymer matrix as described above.

If a molar excess of a polyelectrophilic component is used, the resulting matrix has a net negative charge and can be used to ionically bind and deliver positively charged compounds. Examples of positively charged compounds that can be delivered from these matrices include various drugs, cells, proteins, and polysaccharides. Positively charged collagens, such as methylated collagen, and glycosaminoglycan derivatives such as esterified deacetylated hyaluronic acid, esterified deacetylated desulfated chondroitin sulfate A, esterified deacetylated desulfated chondroitin sulfate C, deacetylated desulfated keratan sulfate, deacetylated desulfated keratosulfate, esterified desulfated heparin, and chitosan, can be effectively incorporated into the crosslinked polymer matrix as described above.

Delivery of Cells and Genes

The crosslinked polymer compositions of the present invention can also be used to deliver various types of living cells or genes to a desired site of administration in order to form new tissue. The term "genes" as used herein is intended to encompass genetic material from natural sources, synthetic nucleic acids, DNA, antisense-DNA and RNA.

When used to deliver cells, for example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

The cells or genes may be either allogeneic or xenogeneic in origin. For example, the compositions can be used to deliver cells or genes from other species that have been genetically modified. Because the compositions of the invention are not easily degraded in vivo, cells and genes entrapped within the crosslinked polymer compositions will be isolated from the patient's own cells and, as such, will not provoke an immune response in the patient. In order to entrap the cells or genes within a crosslinked polymer matrix, the cells or genes are pre-mixed with the polynucleophilic component(s), and then the polyelectrophilic component(s) are added to the mixture to form a crosslinked matrix, thereby entrapping the cells or genes within the matrix. Alternatively, the initial pre-mixing may be carried out with the polyelectrophilic component(s), followed by subsequent addition of the polynucleophilic component(s).

As discussed above for biologically active agents, when used to deliver cells or genes, the synthetic polymers preferably also contain biodegradable groups to aid in controlled release of the cells or genes at the intended site of delivery.

Bioadhesives

As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and either a non-native tissue surface or a surface of a synthetic implant.

In a general method for effecting the attachment of a first surface to a second surface, the reactive composition is applied to a first surface, which is then contacted with a second surface to effect adhesion therebetween. Preferably, all reactive components of the reactive composition are first mixed to initiate crosslinking, then delivered to the first surface before substantial crosslinking has occurred. The first surface is then contacted with the second surface, preferably immediately, to effect adhesion . At least one of the first and second surfaces is preferably a native tissue surface.

The two surfaces may be held together manually, or using other appropriate means, while the crosslinking reaction is proceeding to completion. Crosslinking is typically sufficiently complete for adhesion to occur within about 5 to 60 minutes after mixing of the first and second synthetic polymers. However, the time required for complete crosslinking to occur is dependent on a number of factors, including the type and molecular weight of each reactive component, the degree of functionalization, and the concentration of the reactive composition (i.e., higher concentrations result in faster crosslinking times).

At least one of the first and second surfaces is preferably a native tissue surface. As used herein, the term "native tissue" refers to biological tissues that are native to the body of the patient being treated. As used herein, the term "native tissue" is intended to include biological tissues that have been elevated or removed from one part of the body of a patient for implantation to another part of the body of the same patient (such as bone autografts, skin flap autografts, etc.). For example, the compositions of the invention can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants). For example, the reactive polymer compositions of the present invention can be used to adhere a donor cornea to the eye of a recipient patient.

As used herein, the term "synthetic implant" refers to any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

Ophthalmic Applications

Because of their optical clarity, the crosslinked polymer compositions of the invention are particularly well suited for use in ophthalmic applications. For example, a synthetic lenticule for correction of vision can be attached to the Bowman's layer of the cornea of a patient's eye using the methods of the present invention. As disclosed in commonly assigned U.S. Pat. No. 5,565,519, issued Oct. 15, 1996 to Rhee et al., a chemically modified collagen (such as succinylated or methylated collagen) that is in substantially nonfibrillar form at pH 7 can be crosslinked using a synthetic hydrophilic polymer, then molded into a desired lenticular shape and allowed to complete crosslinking. The resulting crosslinked collagen lenticule can then be attached to the Bowman's layer of a de-epithelialized cornea of a patient's eye using the methods of the present invention. By applying the reaction mixture comprising the first and second synthetic polymers to the anterior surface of the cornea, then contacting the anterior surface of the cornea with the posterior surface of the lenticule before substantial crosslinking has occurred, electrophilic groups on the second synthetic polymer will also covalently bind to collagen molecules in both the corneal tissue and the lenticule to firmly anchor the lenticule in place. Alternatively, the reaction mixture can be applied first to the posterior surface of the lenticule, which is then contacted with the anterior surface of the cornea.

The compositions of the present invention are also suitable for use in vitreous replacement.

Tissue Augmentation

The reactive compositions of the invention can also be used for augmentation of soft or hard tissue within the body of a mammalian subject. As such, they may be better than currently marketed collagen-based materials for soft tissue augmentation, because they are less immunogenic and more persistent. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue.

The compositions of the invention are particularly suited for use as a replacement material for synovial fluid in osteoarthritic joints, serving to reduce joint pain and improve joint function by restoring a soft gel network in the joint. The crosslinked compositions can also be used as a replacement material for the nucleus pulposus of a damaged intervertebral disk. The nucleus pulposus of the damaged disk is first removed, and the reactive composition is then injected or otherwise introduced into the center of the disk. The composition may either be crosslinked prior to introduction into the disk, or allowed to crosslink in situ.

In a general method for effecting augmentation of tissue within the body of a mammalian subject, the components of the reactive composition are injected simultaneously to a tissue site in need of augmentation through a small-gauge (e.g., 25–32 gauge) needle. Once inside the patient's body, the nucleophilic groups on the polynucleophilic component (s) and the electrophilic groups on the polyelectrophilic component(s) react with each other to form a crosslinked polymer network in situ. Electrophilic groups on the polyelectrophilic component(s) may also react with primary amino groups on lysine residues of collagen molecules within the patient's own tissue, providing for "biological anchoring" of the compositions with the host tissue.

Adhesion Prevention

Another use of the reactive compositions of the invention is to coat tissues in order to prevent the formation of adhesions following surgery or injury to internal tissues or organs. In a general method for coating tissues to prevent the formation of adhesions following surgery, the reactive components are mixed and a thin layer of the reaction mixture is then applied to the tissues comprising, surrounding, and/or adjacent to the surgical site before substantial crosslinking has occurred. Application of the reaction mixture to the tissue site may be by extrusion, brushing, spraying (as described above), or by any other convenient means.

Following application of the reaction mixture to the surgical site, crosslinking is allowed to continue in situ prior to closure of the surgical incision. Once crosslinking has reached equilibrium, tissues that are brought into contact with the coated tissues will not adhere thereto. The surgical site can then be closed using conventional means (sutures, etc.).

In general, compositions that achieve complete crosslinking within a relatively short period of time (i.e., 5–15 minutes following admixture of the reactive components) are preferred for use in the prevention of surgical adhesions, so that the surgical site may be closed relatively soon after completion of the surgical procedure.

Coating Material for Synthetic Implants

Another use of the crosslinked polymer compositions of the invention is as a coating material for synthetic implants. In a general method for coating a surface of a synthetic implant, the components of the reactive composition are mixed with an aqueous medium, and a thin layer of the reaction mixture is then applied to a surface of the implant before substantial crosslinking has occurred. In order to minimize cellular and fibrous reaction to the coated implant, the reaction mixture is preferably prepared to have a net neutral charge. Application of the reaction mixture to the implant surface may be by extrusion, brushing, spraying (as described above), or by any other convenient means. Following application of the reaction mixture to the implant surface, crosslinking is allowed to continue until complete crosslinking has been achieved.

Although this method can be used to coat the surface of any type of synthetic implant, it is particularly useful for implants where reduced thrombogenicity is an important consideration, such as artificial blood vessels and heart valves, vascular grafts, vascular stents, and stent/graft combinations. The method may also be used to coat implantable surgical membranes (e.g., monofilament polypropylene) or meshes (e.g., for use in hernia repair). Breast implants may also be coated using the above method in order to minimize capsular contracture.

The compositions of the present invention may also be used to coat lenticules, which are made from either naturally occurring or synthetic polymers.

Treatment of Aneurysm

The reactive compositions of the invention can be extruded or molded in the shape of a string or coil, then dehydrated. The resulting dehydrated string or coil can be delivered via catheter to the site of a vascular malformation, such as an aneurysm, for the purpose of vascular occlusion and, ultimately, repair of the malformation. The dehydrated string or coil can be delivered in a compact size and will rehydrate inside the blood vessel, swelling several times in size compared to its dehydrated state, while maintaining its original shape.

Other Uses

As discussed in commonly assigned U.S. Pat. No. 5,752,974, issued May 19, 1998 to Rhee et al., the reactive polymer compositions of the invention can be used to block or fill various lumens and voids in the body of a mammalian subject. The compositions can also be used as biosealants to seal fissures or crevices within a tissue or structure (such as a vessel), or junctures between adjacent tissues or structures, to prevent leakage of blood or other biological fluids.

The compositions can also be used as a large space-filling device for organ displacement in a body cavity during surgical or radiation procedures, for example, to protect the intestines during a planned course of radiation to the pelvis.

The compositions of the invention can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture is preferably applied to the interior surface of the vessel (for example, via catheter) immediately following mixing of the first and second synthetic polymers. Because the compositions of the invention are not readily degradable in vivo, the potential for restenosis due to degradation of the coating is minimized. The use of crosslinked polymer compositions having a net neutral charge further minimizes the potential for restenosis.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. All patents, patent applications, patent publications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Preparation of a Two-Component Tissue Sealant Composition a. First Component

Pentaerythritol poly(ethylene glycol)ether tetra-succinimidyl glutarate ("SG-PEG") (mol. wt. 10,000) is dissolved in 0.5 mM sodium phosphate pH 6.0 at a concentration of 20% w/v. (This solution is not stable in aqueous media due to the susceptibility of the active ester to hydrolysis and should be used within one hour of preparation).

b. Second Component

Pentaerythritol poly(ethylene glycol)ether tetra-sulfhydryl (mol. wt. 10,000) is dissolved in 300 mM sodium phosphate/sodium carbonate buffer ("P/C buffer"), pH 9.6, at a concentration of 20% w/v. P/C buffer is prepared as follows: 300 mM sodium monobasic phosphate is mixed with 300 mM sodium carbonate to achieve pH 9.6. The final molarity is approximately 117 mm phosphate and 183 mM carbonate. This solution is stable in aqueous media, but care should be taken to prevent the exposure of the solution to oxygen to prevent oxidation to disulfide. Although pH is preferred for certain compositions, a pH of 8 to 10.5 is generally believed to be suitable for use in the practice of the present invention.

Example 2

Surgical Sealing of Arteries

The right carotid artery of New Zealand white rabbits is exposed. The rabbits are treated with 200 U/kg of heparin and the vessel is clamped proximally and distally using atraumatic vascular clamps. A puncture hole is made in the carotid artery using a 27G needle. The control rabbits are treated with tamponade until hemostasis is achieved. For the treated rabbits, approximately 0.5 mL of each of the two components of the compositions prepared as described in Example 1 are delivered to the defect site using a two component sprayer (Duo Flow, Hemaedics, Malibu, Calif.). After the material is allowed to set for 30 sec, the clamps are removed and the time to hemostasis and the blood loss are measured. The arteries of the control rabbits also remain clamped for 30 sec for consistency. The results are shown in Table 3.

TABLE 3

Blood Loss and Time to Hemostasis as a Function of Treatment

| Treatment | Blood Loss (g) | Time to Hemostasis (sec) |
|---|---|---|
| Tamponade (n = 18) | 5.7 ± 3.4 | 144 ± 34 |
| Gel (n = 17) | 1.0 ± 2.5 | 31 ± 65 |

The above results illustrate that the composition significantly reduces the amount of blood loss and time to hemostasis from a punctured artery.

Example 3

Surgical Sealing of an ePTFE Graft

The dogs are treated with heparin to achieve an activated clotting time of greater than 480 sec. The left iliac of the dogs is exposed and isolated using atraumatic vascular clamps placed distally and proximally. A 5 cm segment of the artery is excised and replaced with an ePTFE (polytetrafluoroethylene) graft of the same diameter. Prior to the completion of the anastamosis, the graft was de-aired using a 27G needle. Approximately 3.0 mL of each of the two components of the composition prepared according to Example 1 is delivered to the defect site using a two-component sprayer (Cohesion Technologies, Inc., Palo Alto, Calif.). After the material is allowed to set for 30 sec, the clamps are removed and the time to hemostasis and the blood loss are measured. The procedure was repeated on the left iliac, with the exception of material application. The right iliac received only tamponade treatment. The results are shown in Table 4.

TABLE 4

Blood Loss and Time to Hemostasis as a Function of Treatment

| Treatment | Blood Loss (g) | Time to Hemostasis (sec) |
|---|---|---|
| Tamponade (n = 2) | 244, 180 | >15, >15 |
| Gel (n = 2) | 18, 7 | 3.3, 2.3 |

The above results illustrate that this composition significantly reduces the amount of blood loss and time to hemostasis from an ePTFE anastamosis.

Example 4

Enhanced Biocompatibility of Thioester-linked Formulations

Up to six subcutaneous pockets are made on the backs of New Zealand white rabbits. Approximately 1.0 mL of each of the components of the composition described in Example 1 is delivered to the defect site using a two-component sprayer (Cohesion Technologies, Inc., Palo Alto, Calif.) for liquid formulations or a spatula for formulations that are gelled ex-vivo. The grading key is shown in Table 5 and the results are shown in Table 6.

TABLE 5

Grading Key for Biocompatibility Experiments

| Score | Gross Observations | Histological Observations |
|---|---|---|
| − | all tissues appeared normal | all tissues appeared normal, no inflammation |
| + | mild foreign body response | mild inflammation |
| ++ | moderate foreign body response | moderate inflammation |
| +++ | marked foreign body response | marked inflammation |
| ++++ | severe foreign body response | severe inflammation |

TABLE 6

Results for Biocompatibility Experiments

| Test | Description | Results | |
|---|---|---|---|
| | | Gross Observations | Histological Observations |
| A | surgical control | − | + |
| B | fibrillar collagen | − | + |
| C | 20% w/v tetra-SG PEG 10,000 + 20% w/v tetra-amino PEG 10,000 | ++++ | ++++ |
| D | 20% w/v tetra-SG PEG 10,000 + 20% w/v tetra-sulfhydryl PEG 10,000 | ++ | ++ |
| E | 20% w/v tetra-SG PEG 10,000 + 20% w/v tetra-amino PEG 10,000; gelled ex-vivo; treated with mono-SG PEG 5000 | + | ++ |
| F | 20% w/v tetra-SG PEG 10,000 + 20% w/v di-sulfhydryl PEG 3,400; gelled ex-vivo; treated with di-amino PEG 3400 | ++++ | ++++ |

Experiments A and B show a mild gross and histological response of fibrillar collagen (Collagen Corporation, Palo Alto, Calif.) and the surgical control. Experiment C shows a severe response to gels made with amino-PEG. The response consists of thick encapsulation of the gel and abscess formation. By substitution of sulfhydryl-PEG for amino-PEG, as in Experiment D, the biocompatibility of the gel is significantly improved. Experiment E involves forming an amino gel ex-vivo and incubating the gel in a solution of mono-SG PEG, 5000 mol. wt. During the incubation period, the mono-SG PEG reacts with the free amines present on the gel network, thus reducing the amount of free amines on the polymeric network. This treatment enhances the biocompatibility of the gel. Experiment F involves forming a sulfhydryl gel ex-vivo and incubating the gel in a solution of mono-SG PEG, 5000 mol. wt. During the incubation period, the di-amino, PEG reacts with the free SG groups present on the gel network, thus increasing the amount of free amines on the polymeric network. This treatment decreases the biocompatibility of the gel. Thus, these results show the enhanced biocompatibility of sulfhydryl formulations over amino formulations.

Example 5

Effect of Buffer and Reactive Group on Gel Times

A desirable characteristic of the compositions described herein is their ability to rapidly achieve gelation. In this experiment, the effects of buffer strength and composition on gelation kinetics are studied. For all experiments, the tetra-functional SG PEG described in Example 1 is dissolved in 0.5 mM sodium phosphate, pH 6.0, and the tetra-sulfhydryl PEG described in Example 1, or the equivalent tetra-amino PEG is dissolved in the buffer listed in Table 7.

TABLE 7

Effect of Phosphate vs. Carbonate Buffer on Amino and Sulfhydryl Formulations

| Test | Formulation | Buffer | Gel Time (sec) |
|---|---|---|---|
| A | 10% w/v tetra-SG PEG 10,000 + 10% w/v tetra-amino PEG 10,000 | 300 mM dibasic sodium phosphate pH 9 | 16 |
| B | 10% w/v tetra-SG PEG 10,000 + 10% w/v tetra-sulfhydryl PEG 10,000 | 300 mM dibasic sodium phosphate pH 9 | 55 |
| C | 10% w/v tetra-SG PEG 10,000 + 10% w/v tetra-amino PEG 10,000 | 300 mM sodium carbonate pH 9 | 14 |
| D | 10% w/v tetra-SG PEG 10,000 + 10% w/v tetra-sulfhydryl PEG 10,000 | 300 mM sodium phosphate pH 9 | 9 |
| E | 10% w/v tetra-SG PEG 10,000 + 10% w/v tetra-sulfhydryl PEG 10,000 | P/C Buffer pH 9.6 | 3 |

Experiments A and B show the difference in gel times in amino formulations and sulfhydryl formulations in phosphate buffer. In this buffer, an increase in gelation rate is observed for sulfhydryl formulations compared to amino formulations. Experiments C and D show the difference in gelation times in amino formulations and sulfhydryl formulations in carbonate buffer. As shown, a decrease in gel time is observed for sulfhydryl formulations in carbonate buffer. In the preferred P/C Buffer, a gel time of 3 seconds is observed.

Example 6

Rheometric Measurements

The first component (tetra-functional Sulfhydryl-PEG, 10,000 mol. wt.) was prepared according to Example 1 and suspended in P/C Buffer. The second component (tetra-functional SG-PEG, 10,000 mol. wt.) was prepared according to Example 1 in 0.5 mM phosphate, pH 6.0. The two components (0.6 ml each) were loaded in a dual-syringe device with joiner and cannula. The cannula contained a mixing element. The solutions were mixed, and the resultant mixture was immediately delivered into a parallel plate cell of a Rheometrics Fluids Spectrometer 8500 (Rheometrics, Inc., Piscataway, N.J.). The upper platen had a diameter of 25 mm, and the gap between upper and lower parallel plates was 1.5 mm.

Figure 3:
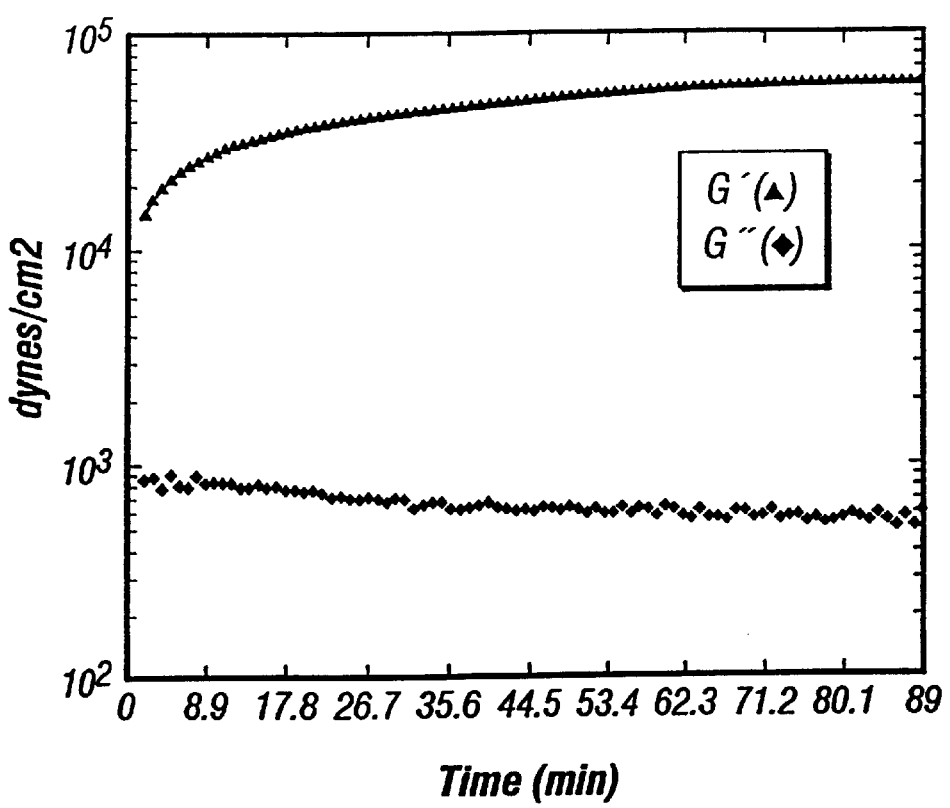
FIG. 3 is a graph indicating the results of a rheometric evaluation of gelation of a mixture of reactive tetrafunctional polyethylene glycols, as described in Example 6.

Gelation began immediately upon mixing of the formulation. The instrument was started, and G' and G" (elastic and viscous moduli, respectively) were measured at 1% strain and 1 radian/sec. In less than a minute, G' was near $10^4$ dyneS/$CM^2$, which is characteristic of a soft rubbery material. G' began to plateau within 15 min, and continued to rise very gradually for more than an hour afterwards. G" was in the order of $10^2$ dynes/$cm^2$, and declined gradually. These results are consistent with a rapidly gelling material. G' and G" for the unreacted starting materials was about 1–10 dynes/$cm^2$. These results are depicted in FIG. 3.

Measurements of the elastic (G') and viscous modulus (G") as a function of time can still be made, and the kinetics of gelation can be followed. As indicated in this experiment, a G' of greater than $10^2$ dynes/$cm^2$ in less than one minute indicates rapid gelation.

Example 7

Effects of Buffers on Gel Time Using Sulfhydryl-PEG and N-hydroxy-succinimidyl-PEG (NHS-PEG)

All tests were done with 50 ml of 20% (w/v) 4 arm, 10,000 mol. wt., tetrafunctional SG-PEG mixed with 50 ml of 20% (w/v) 4 arm, 10,000 mol. wt., tetra-functional sulfhydryl-PEG). Different buffers were used, and the times to gel were noted. The SG-PEG was dissolved in 0.5 mM phosphate, pH 6.0 for all tests. The sulhydryl-PEG was dissolved in the buffers given below at a pH of 9.6 and times to gel are noted.

TABLE 8

Effect of Buffers on Gelation Time

| Test | Buffer | Gel Time (sec) |
|---|---|---|
| A | P/C Buffer | 8 |
| B | 150 mM phosphate | 35 |
| C | 58 mM phosphate 91 mM sodium chloride | 138 |
| D | 58 mM phosphate 91 mM borate | <19 |
| E | 58 mM phosphate 91 mM AMPSO* | 8 |

*(3[1,1-dimethyl-2-hydroxy-ethyl)amino]-2-hydroxypropane-sulfonic acid

As shown, buffers with pKs between 8 and 10.5 (borate, 8.1; carbonate, 10.3; AMPSO, 9.0), and mixtures thereof, are suitable.

Example 8

Sulfhydryl-reactive PEGS

The gelation characteristics of several different formulations are described below:

8a: Gelation of Di Functional Maleimidyl-PEG, 3400 mol. wt. (MAL-PEG) with Tetra-Sulfhydryl PEG, 10,000 mol. wt. A 20% (w/v) solution of MAL-PEG in 0.5 mM sodium phosphate, pH 6.0, was missed rapidly with an equal volume of 20% (w/v) tetra-sulfhydryl PEG in 150 mM sodium phosphate, pH 5.0. Gelation occurred in 15 sec. The gel became a firm, rubbery solid in a minute or less.

8b: Gelation of Difunctional Iodoacetamide PEG, 3,400 mol. wt. ("IAM-PEG") with Tetra-Sulfhydryl PEG. 10,000 mol. wt. LAM-PEG was dissolved at 20% (w/v) in 0.5 mM sodium phosphate, pH 6.0, and mixed rapidly with a 20% (w/v) solution of tetra-sulfhydryl PEG in P/C Buffer sodium phosphate-carbonate, pH 9.6. Gelation occurred in less than 40 sec. A firm gel formed within 2 min.

8c: Gelation of Tetra-Sulfhydryl PEG. 10,000 mol. wt., with Dilute Hydrogen Peroxide. A 20% (w/v) solution of tetra-sulfhydryl PEG in P/C Buffer, was mixed with an equal volume of 0.1% (w/v) hydrogen peroxide. Gelation occurred in 15 sec. A firm gel formed in less than 2 min.

8d: Gelation of Tetra Functional Acrylate PEG, 10,000 mol. wt. (Acr-PEG) with Tetra-Sulfhydryl PEG, 10,000 mol. wt. A 20% (w/v) solution of Acrylate (Acr)-PEG in water was mixed rapidly with an equal volume of 20% (w/v) tetra-sulfhydryl PEG in 300 mM sodium phosphate/sodium carbonate buffer, pH 9.6. Gelation occurred in approximately 15 sec. The gel became a firm, rubbery solid in a minute or less.

8e: Gelation of Tetra Functional Succinimidyl Glutarate PEG, 10,000 mol. wt. (SG-PEG) with Octa-Sulfhydryl PEG, 20,000 mol. wt. A 20% (w/v) solution of SG-PEG in water was mixed rapidly with an equal volume of 10% (w/v) octa-sulfhydryl PEG in 300 mM sodium phosphate/sodium carbonate buffer, pH 9.6. Gelation occurred within 15 sec. The gel became a firm, rubbery solid in a minute or less.

8f: Gelation of Di Functional Acrylate PEG, 700 mol. wt. (DA-PEG700) with Trimethylolpropane tris(3-mercaptopropionate) (3-SH) 398 mol. wt. 2.64 g DA-PEG700 was mixed rapidly with a mixture of 1.00 g 3-SH and 20 mg of a catalyst (T403, Jeffamine). Gelation occurred within two minutes. The gel became a firm, rubbery solid in ten minutes or less.

8g: Gelation of Di Functional Acrylate PEG. 700 mol. wt. (DA-PEG 700) and Di Functional Acrylate Polypropyleneoxide, 900 mol. wt. (DA-PPO 900) with Tri-Sulfhydryl PEG (3-SH), 400 mol. wt. A mixture of DA-PEG700 (0.66 g) and DA-PPO 900 (0.85 g) was mixed rapidly with a mixture of 3-SH (0.50 g) and T403 (10 mg). Gelation occurred within five minutes. The gel became a firm, rubbery solid in twenty minutes or less.

Example 9

Blood Coagulation Activity of Thrombin Incorporated into PEG Compositions

This experiment demonstrates that hemostatic PEG gels containing active thrombin protein can be formed on tissue.

9a: Thrombin Incorporated into Tetra-Sulfhydryl PEG Gelled with Hydrogen Peroxide. 20 mg of tetra-sulfhydryl PEG, 10,000 mol. wt., were dissolved in 80 µl of PC Buffer, and 11 µl of bovine thrombin at 8850 NIH units/ml in 0.72 M sodium chloride (Thrombin topical, USP, Gentrac, Inc., Middleton, Wis.) were added. This solution of tetra-sulfhydryl PEG and thrombin was then mixed with 100 µl of 0.1% (w/v) hydrogen peroxide in water, by stirring rapidly in a 1.5 ml plastic tube. The mixture gelled in less than 40 sec, due to oxidation of the sulfhydryl groups to disulfide bonds. After 1.5 min, the gel was a firm, rubbery solid. On top of this gel was layered 200 µl of rabbit blood plasma. The plasma had been separated from citrated blood and contained approximately 11 mM citrate. Just prior to addition, this citrated blood plasma was re-calcified by addition of 8 µl of 0.5 M calcium chloride, to achieve a concentration of about 20 mM calcium. This re-calcified blood plasma was observed to form a fibrin clot 1.5 minutes after layering onto the PEG gel. The clotting reaction was taken as evidence for the presence of active thrombin in the PEG gel.

When control studies are performed, a second oxidized sulhydryl-PEG gel without thrombin does not clot rabbit plasma until 20 minutes have elapsed. As a further control, re-calcified rabbit plasma is held in an identical plastic tube; and it clots spontaneously after 13 minutes. Therefore, the sulfhydryl-PEG gel without thrombin clots blood no faster than control re-calcified plasma.

When the analogous experiment was attempted with tetra-sulfhydryl PEG and tetra-SG-PEG, plus thrombin, no enhanced clotting time of plasma was observed. Clotting of plasma was delayed beyond 25 minutes. This result is interpreted to indicate that SG-PEG inactivated thrombin, presumably by binding PEG to lysine side chains of thrombin and interfering with its enzymatic activity.

9b: Thrombin Incorporated into IAM-PEG/Sulfhydryl-PEG Gel. 20 mg of tetra-sulfhydryl PEG, 10,000 mol. wt. are dissolved in 80 µl of PC Buffer along with 11 µl of thrombin, as in 9a. above. 20 mg of IAM-PEG are dissolved in 80 µl of 0.5 mM sodium phosphate, pH 6.0. The two solutions are rapidly mixed in a 1.5 ml plastic tube. The mixture has a gel time less than 30 sec and is a rubbery gel by 1.5 minutes. Re-calcified rabbit plasma (200 µl) is layered on top of the gel, and a fibrin clot forms in this plasma in less than two minutes after layering onto the gel. A control reaction without thrombin forms a fibrin clot more than 18 minutes after layering onto the PEG gel. The rapid formation of a fibrin clot in the sample containing thrombin is taken as evidence for the presence of active thrombin in the PEG gel.

9c: Thrombin Incorporated into NEM-PEG/Sulfhydryl PEG Gel. 20 mg of tetra-sulfhydryl PEG, 10,000 mol. wt., is dissolved in 80 µl of 150 mM sodium phosphate, pH 5.0, along with 11 µl of thrombin, as in 9a. above. 20 mg of NEM-PEG are dissolved in 0.5 mM sodium phosphate, pH 6.0. The two solutions are rapidly mixed in a plastic tube. Gelation occurs in 15 sec. 15 µl of P/C Buffer, are layered onto the top of the PEG gel to adjust the pH to 7–9. Then, 200 µl of re-calcified rabbit plasma are added. A fibrin clot formed in 1.5 min. after addition of the plasma. Control gels with no thrombin form a fibrin clot after 30 min. Again, the rapid formation of a fibrin clot in the PEG gel with thrombin is taken as evidence for the presence of active thrombin.

9d: Gelation of Layered Gels with Thrombin. In order to provide a gel formulation from SG-PEG and sulfhydryl-PEG to which thrombin can be added and remain active, a "gel layering" technique can be used. First, the tetra-sulfhydryl-PEG and tetra-SG-PEG gel at 20% solids, prepared according to Example 1 are sprayed onto sheets as described in Example 2. The sheets are coarse fibered collagen hydrated by saline, which simulates a tissue surface. The total volume is approximately 0.5 ml. This formula gels in 18–15 sec. At 16 seconds, a second gel mixture of tetra-sulfhydryl PEG, di-maleimidyl PEG, both at 20% solids, and thrombin (700 NIH units/ml) of total gel mixture, total volume approx. 0.5 ml, are sprayed on top of the first gel. This second gel layer gels at about 2 minutes. At 3 min after the first gel is sprayed, 0.4 ml of re-calcified rabbit blood plasma, prepared as described above are layered on top of the PEG gel. This plasma clots 1.5 minutes after it is layered onto the PEG gel. The formation of a fibrin clot at this early time, compared to a non-thrombin control, is taken as evidence for active thrombin in the PEG gel.

Example 10

Gelation Using Powdered Formulations 10 mg of powdered tetra-SG PEG, 10,000 mol. wt., is spread on the surface of a piece of weighing paper. 10 mg of tetra-sulfhydryl PEG, 10,000 mol. wt., is dissolved in 80 µl of P/C buffer. The sulfhydryl-PEG solution is loaded into a 1 cc syringe with a Haemedics (Malibu, Calif.) spray head and sprayed onto the SG-PEG on the weighing paper. The sprayed fluid is not stirred or mixed. It begins to gel in 27 seconds and forms a firm, rubbery layer by 2 min. This test shows that components in powdered form are also suitable for use in the present invention.

Example 11

Collagen-containing Compositions

Methylated collagen is prepared by the following process: bovine corium collagen is solubilized using pepsin and purified as described in U.S. Pat. No. 4,233,360. This purified, solubilized collagen is precipitated by neutralization into 0.2M sodium phosphate, pH 7.2. The precipitate is isolated by centrifugation to a final concentration of 70 mg/ml. The material is dried for two days, and then pulverized. Dry methanol containing HCl (to 0.1 N) is added (40 ml) and stirred for four days. Collagen is separated from the acidic methanol, vacuum dried and sterilized by irradiation. The final product is dissolved in water at a pH of 3–4.

For delivery as a sealant, 10 mg of the methylated collagen, 100 mg of tetra-functional sulfhydryl-PEG, 10,000 mol. wt., and 100 mg of tetra-functional SG PEG, 10,000 mol. wt., are dissolved in water at pH 3–4 to a final volume of 1 ml (first component). The second component is 1 ml of P/C Buffer. Each component is placed in a syringe and mixed and sprayed on the desired test site using a dual-syringe delivery system as described in Example 1. The applied mixture gels in less than 3 seconds.

The adhesive and cohesive properties of the gel are examined in a burst test. This test is conducted on a pressure gauge apparatus (PSI-Tronix, Model PG5000, Tulare, Calif.) connected by a pressure line to a circular sample plate with a 2 mm diameter central orifice. Sealant formulations are sprayed onto the plate to seal the orifice. To simulate bonding of the formulations to tissue, the sample plate has a circular sheet of coarse-fibered collagen fastened to it, with a 2 mm hole pierced into it and displaced 2–3 min from the sample plate orifice. Burst strength is measured as a function of the pressure it takes to force saline at a flow rate of 5 ml/min through the sealant gel.

The results are given below in Table 9.

TABLE 9

Burst Strength Measurements of Collagen-Containing Compositions

| Material | Burst Strength, mm Hg |
|---|---|
| Sulfhydryl-PEG/SG-PEG | 100–180 |
| Sulfhydryl-PEG/SG-PEG/Methylated Collagen | 122–205 |

Both formulations have gel times less than 3 seconds. As shown above, the addition of collagen to the formulation enhances burst strength.

Example 12

Synthesis of "12-arm" PEG Compounds

Figure 4A:
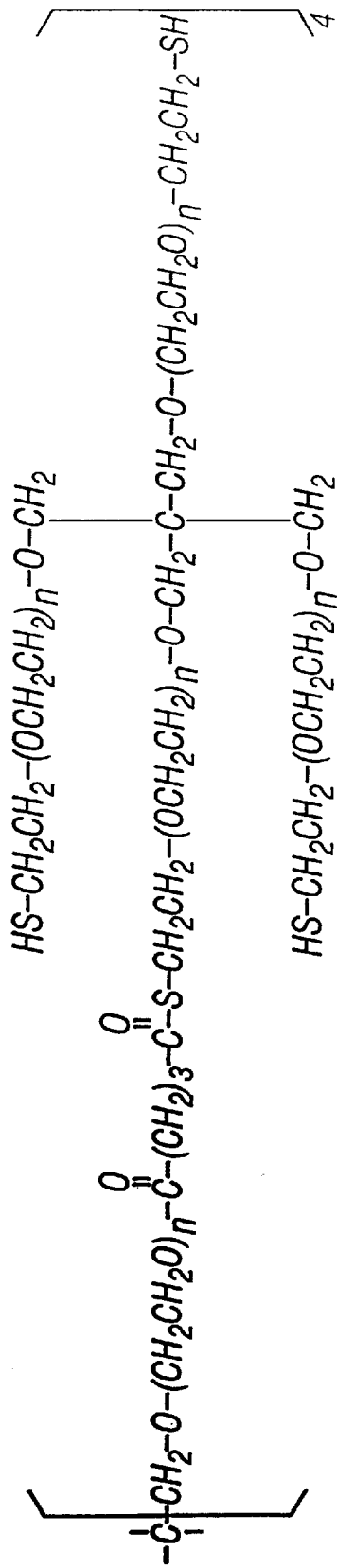
FIG. 4a depicts a "12-arm" sulfhydryl-reactive PEG compound as described in Example 12.
Figure 4B:
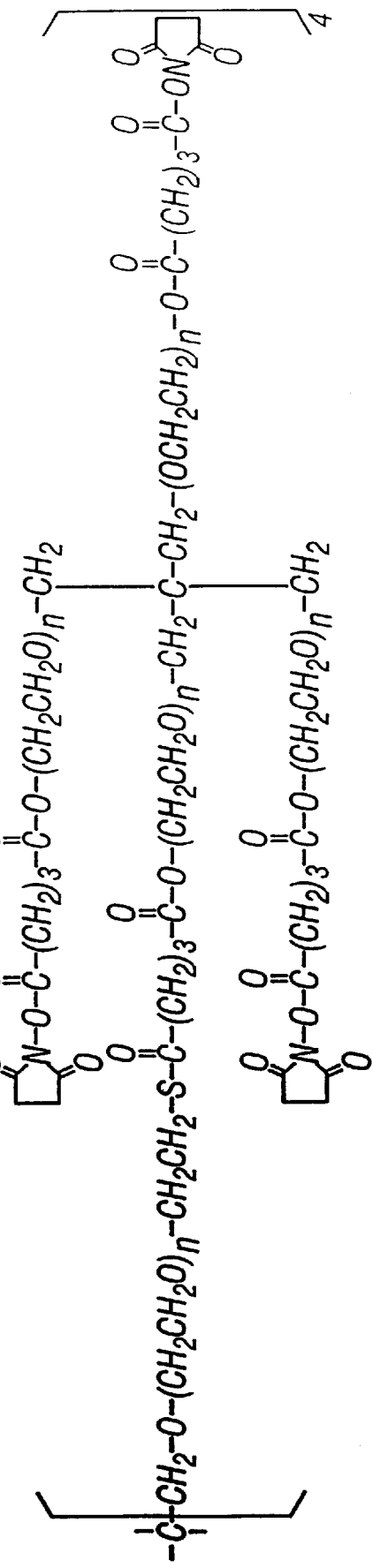
FIG. 4b depicts a "12-arm" succinimidyl reactive PEG compound as described in Example 12.
Figure 5A:
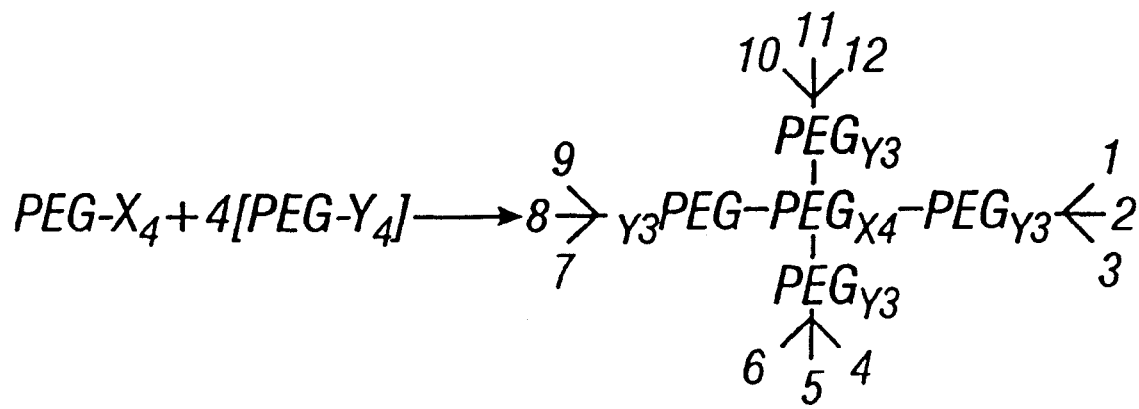
FIGS. 5a and 5b depict the formation of two "12-arm" PEG compounds from "4-arm" intermediates as described in Example 12.
Figure 5B:
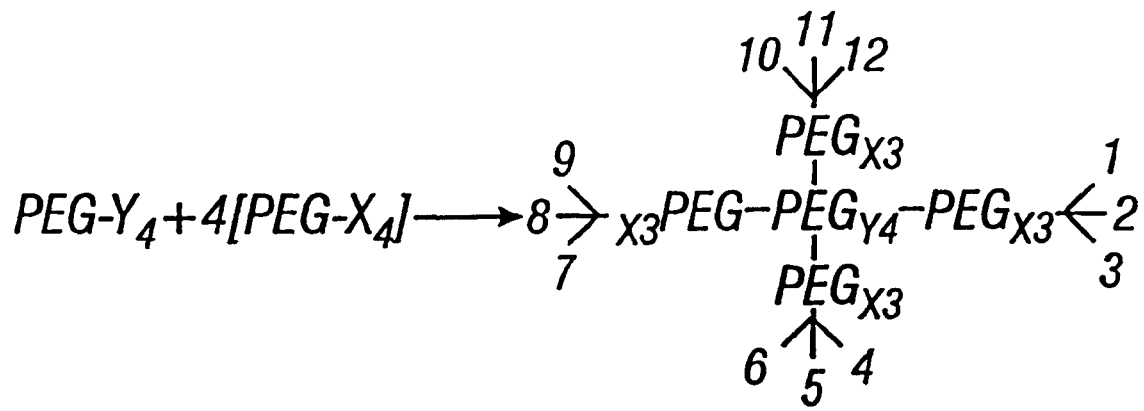

A 12-arm electrophilic PEG compound is formed from 1 mole of 4-arm sulfhydryl PEG, 10,000 mol. wt., and 4 moles of 4-arm SG-PEG, 10,000 mol. wt. The resulting compound is depicted in FIG. 4a. As shown, the compound core is pentaerythritol PEG ether tetra-sulfhydryl and the end functional group is succinimide. As long as the functional groups are reactive with one another to form chemical bonds, the sulfhydryl group, X, can be replaced with other nucleophilic groups, such as $NH_2$, etc., and the succinimidyl group, Y, can be replaced with other electrophilic groups, such as maleimide, carbonyl imidazole, or isocyanate. This method is also used to prepare the 12-arm nucleophilic PEG compound depicted in FIG. 4b by reacting 4 moles of 4-arm sulfhydryl PEG with 1 mole of 4-arm SG-PEG. The formation of these compounds from their respective 4-arm intermediates is also shown in FIG. 5. It should be understood that such reactions produce a heterogeneous population of activated PEG product, some having less than 12 arms, and some having more than 12 arms. As used herein, a "12-arm" PEG also refers to such heterogeneous reaction products that have an average of about 12 arms on each molecule.

12a: 12, Arm Sulfhydryl PEG

Eight grams of pentaerythritol (polyethylene glycol)ether tetra sulfhydryl was dissolved in a mixture of 100 mL of methylene chloride and 100 mL of triethylamine. Two grams of pentaerythritol (polyethylene glycol)ether tetra succinimidyl glutarate in 40 mL of methylene chloride was slowly added with stirring at room temperature under argon overnight. The solvent was removed and the product was isolated by recrystallization in ethanol and dried.

12b: 12 Arm Succinimidyl PEG

Two grams of pentaerythritol (polyethylene glycol)ether tetra succinimidyl glutarate was dissolved in 50 mL of methylene chloride. 0.5 grams of pentaerythritol (polyethylene glycol)ether tetra amine in 10 mL of methylene chloride was slowly added with stirring at room temperature under argon overnight. The solvent was removed and the product was isolated by recrystallization in ethanol and dried.

When the two compounds were tested for burst strength as described in Example 12, they demonstrated a burst strength of greater than 150 mm Hg and a gel time of less than 2 seconds.

We claim:

1. A method for preparing a biocompatible gel, comprising:

(a) forming a reactive composition by admixing a biocompatible crosslinking component A having m sulfhydryl groups with a biocompatible crosslinking component B having n sulfhydryl-reactive groups, wherein m≧2, n≧2 and m+n>4, and further wherein the sulfhydryl-reactive groups are capable of covalent reaction with the m sulfhydryl groups upon admixture of components A and B under effective crosslinking conditions to form a gel in less than one minute; and (b) allowing the components of the reactive composition to crosslink and thereby form a gel.

2. The method of claim 1, wherein the covalent reaction is a nucleophilic substitution reaction.

3. The method of claim 2, wherein step (a) additionally comprises incorporating a polar, hydrophilic solvent into the reactive composition.

4. The method of claim 3, wherein the solvent is a sterile aqueous medium.

5. The method of claim 4, wherein the effective crosslinking conditions comprise providing the reactive composition with an alkaline pH in the range of about 7.5 to about 11.

6. The method of claim 5, wherein the alkaline pH is provided by admixing the components with a base.

7. The method of claim 2, wherein at least one of components A and B is a liquid under the effective crosslinking conditions, and step (a) is carried out without an added solvent.

8. The method of claim 7, wherein the effective crosslinking conditions comprise providing the reactive composition with an alkaline pH in the range of about 7.5 to about 11.

9. The method of claim 8, wherein the alkaline pH is provided by admixing the components with a base.

10. The method of claim 5 or 8, wherein the pH of the reactive composition admixture is in the range of about 8 to about 10.5.

11. The method of claim 2, wherein the pH of the reactive composition is in the range of about 8.5 to about 10.5.

12. The method of claim 1, wherein m+n≧5.

13. The method of claim 12, wherein m≧4 and n≧4.

14. The method of claim 13, wherein m is 4 and n is 4.

15. The method of claim 13, wherein m is 12 and n is 12.

16. The method of claim 13, wherein m is 4 and n is 8.

17. The method of claim 13, wherein m is 8 and n is 4.

18. The method of claim 2, wherein component A has the structural formula (I) and component B has the structural formula (II)

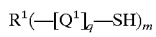 $R^1(-[Q^1]_q-SH)_m$ (I)

 $R^2(-[Q^2]_r-Y)_n$ (II)

wherein:
$R^1$ and $R^2$ are independently selected from the group consisting of $C_2$ to $C_{14}$ hydrocarbyl, heteroatom-containing $C_2$ to $C_{14}$ hydrocarbyl, hydrophilic polymers, and hydrophobic polymers, providing that at least one of $R^1$ and $R^2$ is a polymer;

Y represents one of the n sulfhydryl-reactive groups of component B;

$Q^1$ and $Q^2$ are linking groups;

q and r independently zero or 1; and m and n are as defined previously.

19. The method of claim 18, wherein at least one of $R^1$ and $R^2$ is a hydrophilic polymer.

20. The method of claim 19, wherein the polymer is a synthetic hydrophilic polymer.

21. The method of claim 20, wherein the synthetic hydrophilic polymer is a linear, branched, dendrimeric, hyperbranched, or star polymer.

22. The method of claim 20, wherein the synthetic hydrophilic polymer is selected from the group consisting of polyalkylene oxides; poly(oxyalkylene)-substituted diols; poly(oxyalkylene)-substituted polyols; poly(oxyalkylene)-substituted saccharides; acrylate-based polymers; poly (maleic acid); poly(acrylamide)s; poly(olefinic alcohols); poly(N-vinyl lactams); and copolymers thereof.

23. The method of claim 22, wherein the synthetic hydrophilic polymer is selected from the group consisting of: polyethylene glycol; ethylene oxide copolymers; mono-, di- and tri-polyoxyethylated glycerol; poly(oxyethylene)-substituted polyglycerol; mono- and di-polyoxyethylated propylene glycol; mono- and di-polyoxyethylated trimethylene glycol; polyoxyethylated sorbitol; polyoxyethylated glucose; polyacrylic acid, polymethacrylic acid, poly (hydroxyethylmethacrylate), poly(hydroxyethylacrylate), poly(methylalkylsulfoxide methacrylate)s, poly (methylalkylsulfoxide acrylate)s, and copolymers thereof with additional acrylate species; polymaleic acid; poly (acrylamide); poly(methacrylamide); poly (dimethylacrylamide); poly(N-isopropyl-acrylamide); poly (vinyl alcohol); poly(vinyl pyrrolidone); poly(N-vinyl caprolactam); and copolymers thereof.

24. The method of claim 22, wherein the synthetic hydrophilic polymer is a polyalkylene oxide.

25. The method of 24, wherein the polyalkylene oxide is selected from the group consisting of polyethylene glycol and copolymers of ethylene oxide.

26. The method of claim 25, wherein the polyalkylene oxide is polyethylene glycol.

27. The method of claim 25, wherein the polyalkylene oxide is a copolymer of ethylene oxide and propylene oxide.

28. The method of claim 19, wherein both $R^1$ and $R^2$ are hydrophilic polymers.

29. The method of claim 19, wherein one of $R^1$ and $R^2$ is a hydrophilic polymer and the other is $C_2$ to $C_{14}$ hydrocarbyl containing zero to 2 heteroatoms selected from N, O and S.

30. The method of claim 18, wherein $Q^1$ and/or $Q^2$ contains at least one biodegradable linkage.

31. The method of claim 30, wherein the biodegradable linkage is a hydrolyzable linkage.

32. The method of claim 30, wherein the biodegradable linkage is an enzymatically cleavable linkage.

33. The method of claim 2, wherein the sulfhydryl-reactive groups are selected so as to form a thioester, disulfide, or thioether linkage upon reaction with the sulfhydryl groups.

34. The method of claim 33, wherein the linkage formed is a thioester linkage.

35. The method of claim 34, wherein the sulfhydryl-reactive groups are selected from the group consisting of esters, anhydrides, acid chlorides, ketenes, and isocyanates.

36. The method of claim 35, wherein the sulfhydryl-reactive groups are esters.

37. The method of claim 36, wherein the sulfhydryl-reactive groups are selected from the group consisting of succinimidyl ester and sulfosuccinimidyl ester.

38. The method of claim 33, wherein the linkage formed is a disulfide linkage.

39. The method of claim 38, wherein the sulfhydryl-reactive groups have the structure —S—S—Ar where Ar is a substituted or unsubstituted nitrogen-containing heteroaromatic moiety or a non-heterocyclic aromatic group substituted with an electron-withdrawing moiety.

40. The method of claim 33, wherein the linkage formed is a thioether linkage.

41. The method of claim 40, wherein the sulfhydryl-reactive groups are selected from the group consisting of haloalkyl, haloaryl, epoxy, imino, aziridino, alkynyl, and Michael-type groups containing a carbon-carbon double bond substituted with an electron-withdrawing moiety.

42. The method of claim 41, wherein the sulfhydryl-reactive groups are Michael-type groups containing a carbon-carbon double bond substituted with an electron-withdrawing moiety selected from nitro, halo, carbonyl, and sulfonyl.

43. The method of claim 42, wherein the sulfhydryl-reactive groups are selected from the group consisting of maleimido, ethyleneimino, acrylate, methacrylate, ethenesulfonyl, and α,β-unsaturated aldehydes and ketones.

44. The method of claim 42, wherein the sulfhydryl-reactive groups are selected from the group consisting of maleimido, acrylate and methacrylate.

45. The method of claim 1, wherein the sulfhydryl-reactive groups are selected so as to form said gel in less than 30 seconds.

46. The method of claim 45, wherein the sulfhydryl-reactive groups are selected so as to form said gel in less than 15 seconds.

47. The method of claim 1, wherein a fibrous tensile strength enhancer is incorporated into the admixture in step (a).

* * * * *